(12) United States Patent
Rajagopal

(10) Patent No.: US 11,462,332 B2
(45) Date of Patent: Oct. 4, 2022

(54) SYSTEMS AND METHODS FOR MASS TESTING A POPULATION FOR A CONTAGIOUS INFECTION VIA POOLED SAMPLE TESTING

(71) Applicant: SMART TESTING, LLC, Iowa City, IA (US)

(72) Inventor: Rangaswamy Rajagopal, Iowa City, IA (US)

(73) Assignee: Smart Testing, LLC, Iowa City, IA (US)

(*) Notice: Subject to any disclaimer, the term of this patent is extended or adjusted under 35 U.S.C. 154(b) by 0 days.

(21) Appl. No.: 17/238,275

(22) Filed: Apr. 23, 2021

(65) Prior Publication Data

US 2021/0335501 A1  Oct. 28, 2021

Related U.S. Application Data

(60) Provisional application No. 63/060,322, filed on Aug. 3, 2020, provisional application No. 63/014,423, filed on Apr. 23, 2020.

(51) Int. Cl.
*G16H 50/80* (2018.01)
*G06F 30/20* (2020.01)
*G16H 10/40* (2018.01)

(52) U.S. Cl.
CPC ............ *G16H 50/80* (2018.01); *G06F 30/20* (2020.01); *G16H 10/40* (2018.01)

(58) Field of Classification Search
CPC ........ G16H 50/80; G16H 10/40; G16H 40/67; G16H 50/50; G06F 30/20; Y02A 90/10
See application file for complete search history.

(56) References Cited

U.S. PATENT DOCUMENTS 5,780,222 A * 7/1998 Peddada ................. B01L 3/505
                                                              435/5
2020/0347465 A1  11/2020 Schmidt et al.

OTHER PUBLICATIONS

"Assessment of arbovirus vector infection rates using variable size pooling" Gu et al. Medical and Veterinary Entomology (2004) 18, 200-204 (Year: 2004).*

(Continued)

*Primary Examiner* — Eliza A Lam
(74) *Attorney, Agent, or Firm* — Womble Bond Dickinson (US) LLP

(57) ABSTRACT

Disclosed herein are systems and methods for the mass testing of a population for an infection. Pooled sampling may be used to reduce the number of tests needed for effective community surveillance. Individual members may be sorted into pools via a probability of infection to minimize the tests needed to identify positive individuals. The detection limits of testing assays may be used to help determine an appropriate pool size. Taxonomy tables characterizing the solution space of the total tests needed based on different variables may be generated and/or used to make testing decisions. Simulations of mass testing schemes may be used to facilitate testing decisions. Systems may be used to coordinate data and/or automate one or more steps of the testing process. Long-term community surveillance strategies may use prevalence testing, periodic mass testing via sample pooling, and/or periodic single sample testing to contain the spread of a contagion.

20 Claims, 8 Drawing Sheets

(56) References Cited

OTHER PUBLICATIONS

"Pooling biospecimens and limits of detection: effects on ROC curve analysis" Mumford et al. Biostatistics (2006), 7, 4, pp. 585-598 doi:10.1093/biostatistics/kxj027 Advance Access publication on Mar. 10, 2006 (Year: 2006).*

Arnaout et al., "SARS-CoV2 Testing: The Limit of Detection Matters," bioRxiv, Jun. 4, 2020 (doi: 10.1101/2020.06.02.131144).

Barak et al., "Lessons from applied large-scale pooling of 133,816 SARS-CoV-2 RT-PCR tests," Sci Transl Med, Apr. 14, 2021, 13:eabf2823, 7 pp.

Barber, "Researchers Push for Mass Blood Tests as a Covid-19 Strategy," Wired, Mar. 25, 2020 (available at https://www.wired.com/story/researchers-push-for-mass-blood-test-as-a-covid-19-strategy/).

Chivers, "The obscure maths theorem that governs the reliability of Covid testing," The Guardian, Apr. 18, 2021, 8 pp.

Cleary et al., "Using viral load and epidemic dynamics to optimize pooled testing in resource-constrained settings," Sci Transl Med, Apr. 14, 2021, 13(589):eabf1568, 64pp.

Goethe University Frankfurt, "Pool testing of SARS-CoV-02 samples increases worldwide test capacities many times over," Mar. 30, 2020, 5 pp (available at https://aktuelles.uni-frankfurt.de/englisch/pool-testing-of-sars-cov-02-samples-increases-worldwide-test-capacities-many-times-over/).

IGI Testing Consortium, "Blueprint for a pop-up SARS-CoV-2 testing lab," Nat Biotechnol, Jul. 2020, 38:791-797.

Kleiboeker et al., "SARS-CoV-2 viral load assessment in respiratory samples," J Clin Virol, 2020, 129:104439, 3 pp (doi: 10.1016/j.jcv.2020.104439).

Natarajan et al., "Economics of Screening for Pesticides in Ground Water," JAWRA Journal of the American Water Resources Association, Aug. 1994, 30(4):579-588.

Quest Diagnostics, "SARS-CoV-2 RNA, Qualitative Real-Time RT-PCR (Test Code 39433) Package Insert," FDA, Nov. 12, 2020, 27 pp (available at https://www.fda.gov/media/136231/download).

Rajagopal et al., "Economics of Sample Compositing as a Screening Tool in Ground Water Quality Monitoring," Groundwater Monitoring & Remediation, Mar. 1989, 9(1):186-192 (doi: org/10.1111/j.1745-6592.1989.tb01130.x).

Sanders, "Campus lab takes COVID-19 testing to utility workers, underserved," Berkeley News UC Berkeley, May 13, 2020, 9 pp (available at https://news.berkeley.edu/2020/05/13/campus-lab-takes-covid-19-testing-to-utility-workers-underserved).

Schmidt et al., "Novel multiple swab method enables high efficiency in SARS-CoV-2 screenings without loss of sensitivity for screening of a complete population," Transfusion, 2020, 60:2441-2447.

Tuzman, "Limits of detection for FDA-authorized COVID-19 diagnostics," Biocentury, Apr. 1, 2020 (available at https://www.biocentury.com/article/304801/limits-of-detection-for-fda-authorized-covid-19-diagnostics.

Wang et al., "Limits of Detection of Six Approved RT-PCR Kits for the Novel SARS-coronavirus-2 (SARS-CoV-2)," Clin Chem, Jul. 1, 2020, 66(7):977-979 (doi: 10.1093/clinchem/hvaa099).

Zheng et al., "Viral load dynamics and disease severity in patients infected with SARS-CoV-2 in Zhejiang province, China, Jan.-Mar. 2020: retrospective cohort study," BMJ, Apr. 21, 2020, 369:m1443, 8 pp (doi: 10.1136/bmj.m1443).

\* cited by examiner

| % Infection | # Infected | Single Sample | 4-sample Pool | 8-sample Pool |
|---|---|---|---|---|
| 0.0 | 0 | 8 | 2 | 1 |
| 12.5 | 1 | 8 | 6 | 7 |
| 25.0 | 2 | 8 | 6-10 | 7-11 |

Fig. 3A

| % Infection | # Infected | Single Sample | 4-sample Pool | 8-sample Pool | 16-sample Pool |
|---|---|---|---|---|---|
| 0.00 | 0 | 16 | 4 | 2 | 1 |
| 6.25 | 1 | 16 | 8 | 8 | 9 |
| 12.50 | 2 | 16 | 8-12 | 8-14 | 9-15 |
| 18.75 | 3 | 16 | 8-16 | 8-18 | 9-19 |
| 25.00 | 4 | 16 | 8-20 | 8-22 | 9-23 |

Fig. 3B

| % Infection | # Infected | Single Sample | 4-sample Pool | 8-sample Pool | 16-sample Pool | 32-sample Pool |
|---|---|---|---|---|---|---|
| 0.00 | 0 | 32 | 8 | 4 | 2 | 1 |
| 3.13 | 1 | 32 | 12 | 10 | 10 | 11 |
| 6.25 | 2 | 32 | 12-16 | 10-16 | 10-18 | 11-19 |
| 9.38 | 3 | 32 | 12-20 | 10-22 | 10-24 | 11-25 |
| 12.50 | 4 | 32 | 12-24 | 10-28 | 10-30 | 11-31 |
| 15.63 | 5 | 32 | 16-28 | 16-32 | 14-34 | 15-35 |
| 18.75 | 6 | 32 | 16-32 | 16-36 | 14-38 | 15-39 |
| 21.88 | 7 | 32 | 16-36 | 16-40 | 14-42 | 15-43 |
| 25.00 | 8 | 32 | 16-40 | 16-44 | 14-46 | 15-47 |

Fig. 3C

| % Infection | # Infected | Single Sample | 4-sample Pool | 8-sample Pool | 16-sample Pool | 32-sample Pool | 64-sample Pool |
|---|---|---|---|---|---|---|---|
| 0.00 | 0 | 64 | 16 | 8 | 4 | 2 | 1 |
| 1.56 | 1 | 64 | 20 | 14 | 12 | 12 | 13 |
| 3.13 | 2 | 64 | 20-24 | 14-20 | 12-20 | 12-22 | 13-23 |
| 4.69 | 3 | 64 | 20-28 | 14-26 | 12-28 | 12-30 | 13-31 |
| 6.25 | 4 | 64 | 20-32 | 14-32 | 12-36 | 12-38 | 13-39 |
| 7.81 | 5 | 64 | 24-36 | 18-38 | 16-42 | 16-44 | 17-45 |
| 9.38 | 6 | 64 | 24-40 | 18-44 | 16-48 | 16-50 | 16-51 |
| 10.94 | 7 | 64 | 24-44 | 18-50 | 16-54 | 16-56 | 17-57 |
| 12.50 | 8 | 64 | 24-48 | 18-56 | 16-60 | 16-62 | 17-63 |
| 14.06 | 9 | 64 | 28-52 | 24-60 | 22-64 | 22-66 | 23-67 |
| 15.63 | 10 | 64 | 28-56 | 24-64 | 22-68 | 22-70 | 23-71 |
| 17.19 | 11 | 64 | 28-60 | 24-68 | 22-72 | 22-74 | 23-75 |
| 18.75 | 12 | 64 | 28-64 | 24-72 | 22-76 | 22-78 | 23-79 |
| 20.31 | 13 | 64 | 32-68 | 28-76 | 26-80 | 26-82 | 27-83 |
| 21.88 | 14 | 64 | 32-72 | 28-80 | 26-84 | 26-86 | 27-87 |
| 23.44 | 15 | 64 | 32-76 | 28-84 | 26-88 | 26-90 | 27-91 |
| 25.00 | 16 | 64 | 32-80 | 28-92 | 26-92 | 26-94 | 27-95 |

Fig. 3D

| % Infection | # Infected | Single Sample | 4-sample Pool | 8-sample Pool | 16-sample Pool | 32-sample Pool | 64-sample Pool | 128-sample Pool |
|---|---|---|---|---|---|---|---|---|
| 0.00 | 0 | 128 | 32 | 16 | 8 | 4 | 2 | 1 |
| 0.78 | 1 | 128 | 36 | 22 | 16 | 14 | 14 | 15 |
| 1.56 | 2 | 128 | 36-40 | 22-28 | 16-24 | 14-24 | 14-26 | 15-27 |
| 2.34 | 3 | 128 | 36-44 | 22-34 | 16-32 | 14-34 | 14-36 | 15-37 |
| 3.13 | 4 | 128 | 36-48 | 22-40 | 16-40 | 14-44 | 14-46 | 15-47 |
| 3.91 | 5 | 128 | 40-52 | 26-46 | 20-48 | 18-52 | 18-54 | 19-55 |
| 4.69 | 6 | 128 | 40-56 | 26-52 | 20-56 | 18-60 | 18-62 | 19-63 |
| 5.47 | 7 | 128 | 40-60 | 26-58 | 20-64 | 18-68 | 18-70 | 19-71 |
| 6.25 | 8 | 128 | 40-64 | 26-64 | 20-72 | 18-76 | 18-78 | 19-79 |
| 7.03 | 9 | 128 | 44-68 | 32-70 | 26-78 | 24-82 | 24-84 | 25-85 |
| 7.81 | 10 | 128 | 44-72 | 32-76 | 26-84 | 24-88 | 24-90 | 25-91 |
| 8.59 | 11 | 128 | 44-76 | 32-82 | 26-90 | 24-94 | 24-96 | 25-97 |
| 9.38 | 12 | 128 | 44-80 | 32-88 | 26-96 | 24-100 | 24-102 | 25-103 |
| 10.16 | 13 | 128 | 48-84 | 36-94 | 30-102 | 28-106 | 28-108 | 29-109 |
| 10.94 | 14 | 128 | 48-88 | 36-100 | 30-108 | 28-112 | 28-114 | 29-115 |
| 11.72 | 15 | 128 | 48-92 | 36-106 | 30-114 | 28-118 | 28-120 | 29-121 |
| 12.50 | 16 | 128 | 48-96 | 36-112 | 30-120 | 28-124 | 28-126 | 29-127 |
| 13.28 | 17 | 128 | 52-100 | 42-116 | 38-124 | 36-128 | 36-130 | 37-131 |
| 14.06 | 18 | 128 | 52-104 | 42-120 | 38-128 | 36-132 | 36-134 | 37-135 |
| 14.84 | 19 | 128 | 52-108 | 42-124 | 38-132 | 36-136 | 36-138 | 37-139 |
| 15.63 | 20 | 128 | 52-112 | 42-128 | 38-136 | 36-140 | 36-142 | 37-143 |
| 16.41 | 21 | 128 | 56-116 | 46-132 | 42-140 | 40-144 | 40-146 | 41-147 |
| 17.19 | 22 | 128 | 56-120 | 46-136 | 42-144 | 40-148 | 40-150 | 41-151 |
| 17.97 | 23 | 128 | 56-124 | 46-140 | 42-148 | 40-152 | 40-154 | 41-155 |
| 18.75 | 24 | 128 | 56-128 | 46-144 | 42-152 | 40-156 | 40-158 | 41-159 |
| 19.53 | 25 | 128 | 60-132 | 52-148 | 48-156 | 46-160 | 46-162 | 47-163 |
| 20.31 | 26 | 128 | 60-136 | 52-152 | 48-160 | 46-164 | 46-166 | 47-167 |
| 21.09 | 27 | 128 | 60-140 | 52-156 | 48-164 | 46-168 | 46-170 | 47-171 |
| 21.88 | 28 | 128 | 60-144 | 52-160 | 48-168 | 46-172 | 46-174 | 47-175 |
| 22.66 | 29 | 128 | 64-148 | 56-164 | 52-172 | 50-176 | 50-178 | 51-179 |
| 23.44 | 30 | 128 | 64-152 | 56-168 | 52-176 | 50-180 | 50-182 | 51-183 |
| 24.22 | 31 | 128 | 64-156 | 56-172 | 52-180 | 50-184 | 50-186 | 51-187 |
| 25.00 | 32 | 128 | 64-160 | 56-176 | 52-184 | 50-188 | 50-190 | 51-191 |

Fig. 3E

SYSTEMS AND METHODS FOR MASS TESTING A POPULATION FOR A CONTAGIOUS INFECTION VIA POOLED SAMPLE TESTING

CROSS-REFERENCE TO RELATED APPLICATIONS

This application claims the benefit of priority to U.S. Provisional Application No. 63/014,423, filed on Apr. 23, 2020, and U.S. Provisional Application No. 63/060,322, filed on Aug. 3, 2020, each of which is herein incorporated by reference in its entirety.

BACKGROUND

Highly contagious infections, such as the SARS-CoV-2 virus (causing COVID-19), are prone to causing epidemics or pandemics. The COVID-19 pandemic is a poignant example of how such pandemics can rapidly spread across local and national communities as well as across the globe. In addition to therapeutic strategies, strategies for controlling the spread of the contagion within communities of all scales are needed to combat an epidemic or pandemic. Social restrictions (e.g., social distancing, mask wearing, curfews, stay-at-home orders, quarantines, self-isolation, and economic shut-downs) are helpful for slowing the spread of a contagion within a community but are not sustainable long-term and can cause mental, emotional, social, and financial harm to members of a community. The rapid identification of infected individuals within a community, preferably shortly after infection, could allow more confined and targeted uses of social restrictions and better isolation and starvation of the contagion within a community, ultimately leading to containment or elimination of the contagion. However, rapid identification of infected individuals requires mass testing of general populations for the infection, including asymptomatic individuals, so that individuals can be effectively isolated from other members of a community before extensively transmitting the contagion. The cost, time, and resources required for testing every individual or even large numbers of individuals within a community can be prohibitive, particularly if the individuals need to be occasionally retested over the course of a pandemic or epidemic. Therefore, there is a need for improved methods and systems for mass testing of populations that can accommodate for limited testing capacities.

SUMMARY

Disclosed herein are systems and methods for rapid mass testing of populations, which may be used to contain an infection within a population (e.g., prevent the infection rate from increasing or cause the infection rate to decline over time). By rapidly identifying infected individuals within a population having a threshold level of infection, the spread of infection within that population may be controlled by isolating those infected individuals and breaking the chains of transmission. By doing so the spread of a pandemic may be arrested at a community level. Achieving the lowest threshold possible and keeping the community in that state can lead to long-term containment of the spread of infection or even extinction of the contagion. Effective mass testing may comprise coordinated collecting, constructing, processing, and testing samples within a community at every stage of the process. The separation of infectious individuals within a community or economic system undergoing a pandemic from non-infected individuals may allow the effective "reopening" of the community or economic system within, for example, about 2 weeks of employing a mass testing of individuals within the community or economic system. Periodic mass testing following the containment of an infection may keep the infection within manageable limits and eventually starve out the infection from the community.

According to one aspect of the disclosure, disclosed herein is a method for determining and optionally implementing a strategy for testing or screening individuals within a population for an infection. The method involves obtaining an estimate of the infection rate within the population and/or obtaining a limit of detection for an assay used to test for the infection. The method further involves characterizing a solution space for the number of tests needed to identify individuals within the population who are positive for the infection using a pooled sample testing scheme of one or more pool sizes. The solution space may be characterized for a plurality of pool sizes. The selection of pool sizes may be based on the limit of detection and/or the solution space may be specific to the estimated infection rate. The method further involves choosing a testing scheme based on an expected number of tests needed to identify individuals within the population who are positive for the infection. The chosen testing scheme may be single sample testing or a pooled sample testing scheme defined by one of the one or more pool sizes. The method may involve both obtaining an estimate of the infection rate within the population then determining the solution space specific to the estimated infection rate and obtaining a limit of detection for an assay used to test for the infection then selecting a pool size based on the limit of detection.

The selection of pool sizes based on the limit of detection may comprise selecting a maximum pool size determined by the limit of detection and one or more pool sizes less than the maximum pool size. The chosen testing scheme may comprise a pooled sample testing scheme. The method may involve pooling samples obtained from the individuals according to the chosen testing scheme. The method may comprise testing one or more samples obtained from individuals within the population according to the chosen testing scheme.

Characterizing the solution space may involve accessing one or more taxonomy tables of solution spaces. The one or more taxonomy tables may be stored on an electronic database. The taxonomy tables may comprise a minimum number of tests needed for a given testing scheme. The taxonomy tables may comprise a maximum number of tests needed for a given testing scheme. The taxonomy tables may comprise an expected average number of tests need for a given testing scheme. Choosing the testing scheme may involve using a processing device to automatically compare solution spaces and make a determination.

Characterizing the solution space may involve determining an average number of tests needed to identify the positive individuals. The average number may be determined by a simulation of the given pooled testing scheme. The method may involve performing the simulation. Performing the simulation may involve simulating an infection status for a simulated population having at least the same number of members as the population to be tested, wherein each simulated individual is assigned a positive or negative infection status based on a probability set by the estimated infection rate. The simulated individuals may be randomly distributed into simulated pools defined by the one or more pool sizes. For each of the one or more pool sizes, the number of tests that would be needed to identify the simulated positive individuals using a pooled testing strategy defined by the pool size may be determined.

Assigning each simulated individual a positive or negative status may be performed by independently assigning the positive or negative infection status to each individual based on a probability set by the estimated infection rate. Assigning each simulated individual a positive or negative status may comprise randomly assigning a predetermined number of the simulated individuals a positive infection status, wherein the predetermined number is set according to the estimated infection rate and the size of the simulated population. Assigning each simulated individual a positive or negative status may comprise, for each simulated positive individual, independently assigning a simulated infection level from two or more infection levels based on a probability determined from a known distribution of infection levels. A lower portion of the infection distribution comprising between about 10% and about 35% of the distribution may comprise at least two infection classes.

Performing the simulation may further involve identifying and tallying false negatives based on the simulated infection levels within each simulated pool and a predetermined adjusted limit of detection for the pool size. Identifying false negatives may involve assigning a false negative status to the simulated individual and/or simulated pool if the simulated infection level for the individual and/or pool is below the assay's limit of detection and/or adjusted limit of detection, respectively. Identifying false negatives may involve independently assigning a false negative status to the simulated individual and/or simulated pool based on a probability associated with the limit of detection and/or adjusted limit of detection, respectively.

The method may involve sorting the individuals into pools based on a relative probability of infection for each individual. The sorting may be performed in a manner that would minimize the tests needed to identify each positive individual assuming that the ranking of the individuals by their relative probabilities of infection confines all the positive individuals to either a top portion or lower portion of the rankings. The relative probability of infection may be calculated according to one or more factor values obtained for the individuals. The one or more factor values may relate to one or more of personal health, symptoms of infection, risk of exposure, and demographic information.

The method may involve using a processing device to associate unique sample identifiers associated with samples collected from each of the individuals with unique patient identifiers. The method may involve using a processing device to transmit testing instructions to a testing center, optionally to a sample preparation device and/or testing device. The testing instructions may have pool sizes for testing. The testing instructions may have instructions for which samples should be pooled together. The sample preparation device and/or testing device may be configured to automatically prepare samples and/or test samples, respectively, according to the received testing instructions. The method may involve using a processing device to automatically associate positive or negative statuses with each unique sample identifier and/or each unique patient identifier based on received test results. The method may involve using a processing device to automatically perform contact tracing within the population based on identification of positive individuals within the population and a database of individuals within the population According to another aspect of the disclosure, disclosed herein is another method for determining and optionally implementing a strategy for testing or screening individuals within a population for an infection. The method involves obtaining an estimate of the infection rate within the population and estimating a number of infected individuals within the population based on the estimated infection rate and the number of individuals within the population. The method further involves obtaining factor values for a plurality of the individuals for one or more factors indicative of a relative probability of infection. Optionally, the plurality may comprise each of the individuals within the population. The method further involves determining based on the obtained factor values a relative probability of infection for each of the individuals within the plurality of individuals. The method further involves sorting the individuals into an ordered list in which the plurality of individuals is ranked according to probability of infection. The method further involves assigning each of the individuals to a position for an individual sample in one or more hierarchies of an identical first size and first structure based on an order of the ordered list. Each hierarchy has one or more levels of pools of samples. The one or more levels have a base pool at a top level of the hierarchy and two or more mini-pools at each of any additional level below the top level such that each mini-pool is positioned downstream of a single pool at the next higher level. Each mini-pool comprises a subset of the individuals assigned to any upstream pool. Each hierarchy further has individual samples for each individual assigned to the hierarchy at a bottom of the hierarchy. Each individual is assigned to one pool at every level of the hierarchy to which the individual is assigned. For each hierarchy individuals are assigned starting at one end of the hierarchy and proceeding to the other end of the hierarchy so that each individual other than the first individual assigned to the hierarchy is positioned adjacent to the preceding individual from the ordered list and so that each individual other than the last individual assigned to the hierarchy is positioned adjacent to the subsequent individual from the ordered list. For each hierarchy filled, the hierarchy is completely filled with individuals from the ordered list before proceeding to fill another hierarchy. The method involves assigning the individuals to a plurality of hierarchies and/or to a single hierarchy having at least two mini-pools.

The method may further involve characterizing a solution space for the number of tests needed to identify individuals within the population who are positive for the infection using a pooled sample testing scheme of one or more base pool sizes. The pooled sample testing scheme involves testing each base pool for the infection, testing each mini-pool for the infection only if the pool immediately upstream first tests positive for the infection, and testing each individual sample for the infection only if the pool immediately upstream first tests positive for the infection. Characterizing the solution space may involve determining the minimum number of tests needed to identify the infected individuals using a pooled sample testing scheme that assigns each individual to one of the one or more hierarchies. Characterizing the solution space may involve determining the maximum number of tests needed to identify the infected individuals using a pooled sample testing scheme that assigns each individual to one of the one or more hierarchies. Characterizing the solution space may involve determining an expected average number of tests needed to identify the infected individuals using a pooled sample testing scheme that assigns each individual to one of the one or more hierarchies. The expected average number may be determined by a simulation. The minimum number of tests may be less than or equal to the number of individuals within the population. The method may involve determining the entire solution space of tests needed for the estimated infection rate.

The method may involve preparing a pooled sample for one of the pools of the hierarchies from individual samples based on the assigned hierarchy positions of the individuals. The method may involve implementing the pooled sample testing scheme. The method may comprise testing one or more samples obtained from individuals within the population according to the pooled sample testing scheme. The pooled sample testing scheme may be performed only if the minimum number of tests or the expected average number of tests is less than or equal to the number of individuals within the population. Testing for the pooled sample testing scheme may be completed such that each individual is assigned a positive or negative infection status. The hierarchy size may be no greater than a maximum hierarchy size determined according to the limit of detection for an assay to be used in the pooled sample testing scheme.

Each hierarchy may comprise a total of $B^n$ individuals. B may equal 2 and n may be an integer greater than or equal to 3. Each pool may be divided into two downstream mini-pools, except that mini-pools of 4 individuals are positioned directly upstream of the individual samples.

The solution space may be characterized for second set of one or more hierarchies of an identical second size, different from the first size. Characterizing the solution space may involve accessing a taxonomy table characterizing a solution space of tests needed for at least one estimated infection rate and at least hierarchy size. The taxonomy table may characterize the solution space for at least two infection rates and/or at least two hierarchy sizes. The taxonomy table may be automatically accessed from an electronic database in response to input parameters defining the estimated infection rate and population size.

The estimated infection rate may be determined from sampling randomly selected individuals within the population and calculating the infection rate based on the number of positive randomly selected individuals relative to the total number of randomly selected individuals. The assay used for testing may have a limit of detection no greater than about 200 copies/mL. The sampling may involve determining a proportion of the population associated with at least one obtained factor value, wherein the randomly selected individuals comprise a predetermined number of individuals associated with the at least one obtained factor value based on the proportion. The predetermined number may establish a proportion of randomly selected individuals associated with the at least one obtained factor approximately equal to the proportion of the population. The randomly selected individuals may be randomly selected by an automated system comprising a database of individuals within the population. The system may randomly select individuals associated with the at least one obtained factor value. The system may have a database that stores the obtained factor values. The estimated infection rate may be determined by testing comprising pooled sampling. The estimated infection rate may be determined by comparing a test result from one or more pooled samples to simulated distributions of the pooled samples at different infection rates. The samples may be pooled on-site at the time of sample collection.

The relative probability of infection for each individual may be calculated as the sum of a plurality of weighted factor values. The factor values may be values determined based on the response of the individual to one or more questions. The one or more questions may relate to one or more of personal health, symptoms of infection, risk of exposure, and demographic information. The one or more questions may be selected from the list of questions provided in Table 4.

According to another aspect of the disclosure, disclosed herein is another method for determining and optionally implementing a strategy for testing or screening individuals within a population for an infection. The method involves determining a maximum hierarchy size used in a pooled sample testing scheme that assigns each individual to one of one or more hierarchies of identical size and structure. Each hierarchy has one or more levels of pools of samples. The one or more levels have a base pool at a top level of the hierarchy and two or more mini-pools at each of any additional level below the top level such that each mini-pool is positioned downstream of a single pool at the next higher level. Each mini-pool comprises a subset of the individuals assigned to any upstream pool. Each hierarchy further has individual samples for each individual assigned to the hierarchy at a bottom of the hierarchy. Each individual is assigned to one pool at every level of the hierarchy to which the individual is assigned. The maximum hierarchy size is determined by comparing the amount of dilution for an individual sample needed to form a base pool of a predetermined size to the limit of detection for an assay that is to be used to test the base pool.

The method may further involve characterizing a solution space for the number of tests needed to identify individuals within the population who are positive for the infection using a pooled sample testing scheme of one or more base pool sizes. The pooled sample testing scheme involves testing each base pool for the infection, testing each mini-pool for the infection only if the pool immediately upstream first tests positive for the infection, and testing each individual sample for the infection only if the pool immediately upstream first tests positive for the infection. Characterizing the solution space may involve determining the minimum number of tests needed to identify the infected individuals using a pooled sample testing scheme that assigns each individual to one of the one or more hierarchies. Characterizing the solution space may involve determining the maximum number of tests needed to identify the infected individuals using a pooled sample testing scheme that assigns each individual to one of the one or more hierarchies. Characterizing the solution space may involve determining an expected average number of tests needed to identify the infected individuals using a pooled sample testing scheme that assigns each individual to one of the one or more hierarchies. The expected average number may be determined by a simulation. The minimum number of tests may be less than or equal to the number of individuals within the population. The method may involve determining the entire solution space of tests needed for the estimated infection rate.

The method may involve preparing a pooled sample for one of the pools of the hierarchies from individual samples based on the assigned hierarchy positions of the individuals. The method may involve implementing the pooled sample testing scheme. The method may comprise testing one or more samples obtained from individuals within the population according to the pooled sample testing scheme. The pooled sample testing scheme may be performed only if the minimum number of tests or the expected average number of tests is less than or equal to the number of individuals within the population. Testing for the pooled sample testing scheme may be completed such that each individual is assigned a positive or negative infection status.

Each hierarchy may comprise a total of Bn individuals. B may equal 2 and n may be an integer greater than or equal to 3. Each pool may be divided into two downstream mini-pools, except that mini-pools of 4 individuals are positioned directly upstream of the individual samples.

The solution space may be characterized for second set of one or more hierarchies of an identical second size, different from the first size. Characterizing the solution space may involve accessing a taxonomy table characterizing a solution space of tests needed for at least one estimated infection rate and at least hierarchy size. The taxonomy table may characterize the solution space for at least two infection rates and/or at least two hierarchy sizes. The taxonomy table may be automatically accessed from an electronic database in response to input parameters defining the estimated infection rate and population size.

The method may involve obtaining an estimate of the infection rate within the population and estimating a number of infected individuals within the population based on the estimated infection rate and the number of individuals within the population. The estimated infection rate may be determined from sampling randomly selected individuals within the population and calculating the infection rate based on the number of positive randomly selected individuals relative to the total number of randomly selected individuals. The assay used for testing may have a limit of detection no greater than about 200 copies/mL. The sampling may involve determining a proportion of the population associated with at least one obtained factor value, wherein the randomly selected individuals comprise a predetermined number of individuals associated with the at least one obtained factor value based on the proportion. The predetermined number may establish a proportion of randomly selected individuals associated with the at least one obtained factor approximately equal to the proportion of the population. The randomly selected individuals may be randomly selected by an automated system comprising a database of individuals within the population. The system may randomly select individuals associated with the at least one obtained factor value. The system may have a database that stores the obtained factor values. The estimated infection rate may be determined by testing comprising pooled sampling. The estimated infection rate may be determined by comparing a test result from one or more pooled samples to simulated distributions of the pooled samples at different infection rates. The samples may be pooled on-site at the time of sample collection.

The method may involve obtaining factor values for a plurality of the individuals for one or more factors indicative of a relative probability of infection. The relative probability of infection for each individual may be calculated as the sum of a plurality of weighted factor values. The factor values may be values determined based on the response of the individual to one or more questions. The one or more questions may relate to one or more of personal health, symptoms of infection, risk of exposure, and demographic information. The one or more questions may be selected from the list of questions provided in Table 4.

According to another aspect of the disclosure, disclosed herein is a system for minimizing the number of tests needed to test individuals within a population for an infection. The system comprises a memory and a processing device operatively coupled to the memory. The processing device is configured to perform one or more steps of any one of methods described herein, including the aforementioned methods.

According to another aspect of the disclosure, disclosed herein is a system comprising a processing device operatively coupled to a memory and one or more of: one or more first remote electronic devises, a second remote electronic device, a sample preparation device, and a testing device. The system may be configured to perform one or more steps of any one of methods described herein, including the aforementioned methods.

The one or more first remote electronic devises may be operatively coupled in a network with the processing device. The processing device may be programmed to receive data from the one or more remote electronic devices. The processing device may be programmed to store the data to one or more databases. The processing device may be programmed to position one or more individuals within a population into a hierarchy position. The data receivable by the processing device may comprise at least one of: a factor value indicative of a relative probability of infection for an individual, a factor value indicative of a relative probability of infection for the population, a size of the population, a unique identifier for an individual within the population, a unique identifier for the population, one or more unique sample identifiers for collected samples, and an estimated infection rate. The processing device may be configured to transmit data to one or more remote electronic devices. The transmitted data may comprise at least one of: an individual test result, test results for the population, and an estimated infection rate for the population.

The second remote electronic device may be programmed to receive testing instructions. The testing instructions may comprise instructions for pooling individual samples. The processing device may be programmed to associate unique sample identifiers for the samples to be tested to unique individual identifiers identifying the individuals from which the samples were collected. The sample preparation device may be an integral device with the second remote electronic device.

The sample preparation device may comprise robotic pipetting or liquid handling machinery configured for preparing pooled samples for testing. The sample preparation device may be a remote device. The sample preparation device may be programmed to sort samples and/or pool samples according to testing instructions received from the processing device.

The testing device may be configured for detection of a signal generated by an assay for an infection. The testing device may be a remote device. The testing device may be a PCR machine (e.g., an RT-PCR machine). The processing device may be programmed to receive raw data or test results from the detection device for the samples tested and associate test results to individuals. The processing device may be configured to store test results for each sample and/or each individual in a database. The processing device may be configured to calculate an infection rate within a tested population. The testing device may be an integral device with the sample preparation device.

The memory may comprise one or more of the following databases: a database of individuals, a database of populations, a database of samples, a database of hierarchies, a database of test results, a database of simulation results, a database of testing facilities, a database of testing machines, and a database of assays.

The processing device may be configured to associate unique sample identifiers with unique patient identifiers based on information received from a first remote electronic device belonging to a first party. The processing device may be configured to associate unique sample identifiers with positions in one or more hierarchies for the pooled sample testing scheme. The processing device may be configured to transmit testing instructions to a second remote electronic device belonging to a second party different from the first party. The testing instructions may comprise instructions for pooling samples based on unique sample identifiers. The testing instructions may comprise computer readable code executable by the sample preparation device and/or the testing device.

The sample preparation device and/or the testing device may be programmed to identify unique sample identifiers on the samples. The sample preparation device and/or the testing device may comprise a bar-code reader or RFID reader for identifying the unique sample identifiers.

The system may further comprise an assay for producing the detectable signal that can be read by the testing device.

The system may comprise the one or more first remote electronic devices and at least one of the second remote electronic device, the sample preparation device, and testing device. The system may comprise each of: the one or more first remote electronic devices, the second remote electronic device, the sample preparation device, and the testing device.

In any of the aforementioned aspects, the infection may be SARS-CoV-2 or any other suitable infection.

It will be understood that unless dictated otherwise by context, any of the features associated with any of the embodiments or aspects of the disclosure described herein may be combined with other embodiments or aspects where compatible (e.g., either substituting for one or more features thereof or adding to the features thereof) without departing from the scope of this disclosure.

BRIEF DESCRIPTION OF THE DRAWINGS

FIG. 2A illustrates a scenario for one positive individual (represented by the darkened virion symbol). FIG. 2B illustrates a best-case scenario for 4 infected individuals. FIG. 2C illustrates a worst-case scenario for 4 infected individuals.

FIGS. 3A-3E depict examples of taxonomy tables characterizing the solution space of total required tests (TRT) to identify the positive individuals in a population for different hierarchy sizes (base pool sizes) and infection rates (from 0-25%). The total population size in each table is equal to the size of the largest hierarchy. The infection rate determines the number of infected individuals in the population. The population is presumed to be evenly distributed into one or more hierarchies of the defined size such that each individual is assigned to one hierarchy. The hierarchies each comprise $2^n$ individuals where n=2, 3, 4, 5, 6, or 7 for the 4-sample, 8-sample, 16-sample, 32-sample, 64-sample, and 128-sample hierarchies, respectively. Each hierarchy uses a branch number of B=2, except that 4-member pools are divided directly into the 4 constituent individuals, as in FIGS. 2A-2C. FIGS. 3A-3E illustrate taxonomy tables for total population sizes of 8, 16, 32, 64, and 128 individuals, respectively.

FIG. 6A depicts results from the simulation using a pool size of 16 individuals; FIG. 6B depicts results from the simulation using a pool size of 32 individuals.

DETAILED DESCRIPTION

Figure 1:
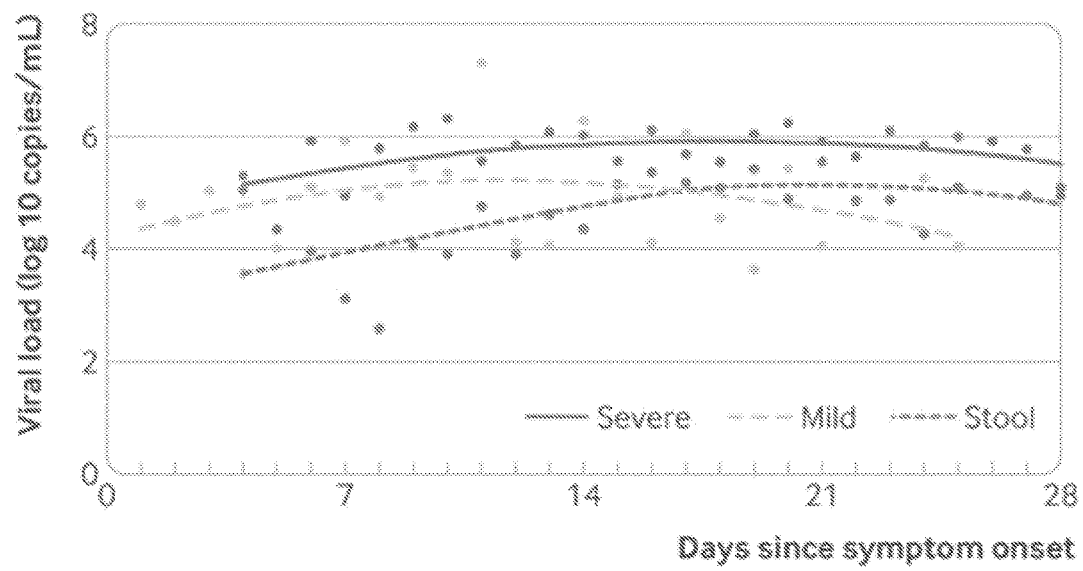
FIG. 1 depicts varying levels of SARS-CoV-2 detected in different sample types at various days since symptom onset.

Disclosed herein are systems and methods of testing that may be used for monitoring or surveilling a community for an infection, referred to herein as community surveillance. Community surveillance may be member-specific in that individual members of the community may be identified as (e.g., inferred to be) positive or negative for the infection. Identification of infected individuals within a community may allow implementation of more efficient strategies for isolating the contagion within the community and controlling the spread of the contagion among the community. Community surveillance may comprise the mass testing of a population. Mass testing may comprise the sampling of large numbers of individuals from a population or community as described elsewhere herein. Generally, mass testing of the population is member-specific (i.e., provides member-specific results). Testing performed for community surveillance may also not be member-specific. For example, prevalence testing may be performed as part of a community surveillance strategy. Prevalence testing may be performed to determine the general prevalence (e.g., an estimated rate of infection) within the community. Prevalence testing may comprise the sampling of a smaller number of individuals from the population than would otherwise be sampled for a round of "mass testing" within the population (e.g., such as member-specific mass testing). Prevalence testing may or may not be member-specific (i.e., may or may not produce member-specific results for the members that are sampled). The testing strategies disclosed herein may employ periodic rounds of mass testing and/or prevalence testing as part of a community surveillance strategy.

Periodic member-specific mass testing is advantageous because it allows for the identification of both symptomatic and asymptomatic individuals, such that asymptomatic individuals do not continue to spread the infection due to an unknown positive infection status. Asymptomatic individuals are individuals who are infected with a contagion yet show no external symptoms (such as, for COVID-19, dry cough, fever, diarrhea, loss of smell or taste, etc.). Asymptomatic individuals are potential spreaders of a contagion and the rapid identification, isolation, and, if necessary, treatment can help effectively contain the spread of a contagion. Symptomatic individuals present one or more symptoms of infection, such as, for COVID-19, dry cough, fever, diarrhea, or impact on their sense of smell or taste. Because symptomatic individuals have a higher chance of being infected, they are often tested first under conventional testing strategies. If positive, infected individuals for particular infections such as COVID-19 are generally recommended to isolate themselves or may need to be hospitalized depending on the severity of the infection. Recovery rates for COVID-19 are high and survivors do gain some immunity.

By way of example, the systems and methods disclosed herein may provide for the identification of 5 asymptomatic infected individuals in a community of 1,000 people by running approximately 150 tests. Effective periodic mass testing enables local, state, federal, private, collegiate and hospital-based laboratories and instrument manufacturers to focus their efforts on two key complementary issues: containing the viral spread (both present and future) and treatment of infected individuals. Additionally, periodic mass testing is likely to identify infected individuals earlier in the infection life cycle and the early identification of an infection in an individual generally leads to better care and treatment outcomes, which likewise may save additional costs.

Effective mass testing, particularly periodic mass testing, may be limited by testing capacity. Testing capacity may be limited by test costs, personnel, and/or the time it takes to process test results. Even if costs are not prohibitive, the time it takes to process high numbers of tests may delay reporting of test results, allowing positive individuals to spread the infection during the delay. The systems and methods disclosed herein may be used to better identify (e.g., infer) the presence of an infection of interest within members of a population of interest and/or to monitor or surveil the spread of an infection of interest within a population of interest. A "community" or "population" as used herein, may generally be considered to comprise individuals within some level of geographic proximity to each other such that members of the community may, at least on occasion, come into sufficient contact with each other to spread a contagion to one another. Communities may be defined by some governing mechanism. For example, a community may comprise an educational institution (such as K-12 school districts, colleges or universities), first responder or essential worker organizations (e.g., healthcare, certain commercial businesses, and both public and private institutions, particularly those which may be critical/central to an economy), or other systems of people or populations described herein. The systems and methods described herein may be particularly advantageous in reducing the number of tests that are needed to identify infected individuals in a population, thereby reducing the time and cost to perform member-specific mass testing of a population and offsetting the constraints that testing capacity may otherwise impose on containing the spread of an infection within a population.

Infection of Interest

The infection of interest may be any contagious infection that is readily transmissible or communicable between members of a population. Infections result from the invasion of an organism's body by pathogens (e.g., viruses or bacteria). In some embodiments, the infection of interest may be a viral infection. Viral infections, in particular, may be readily transmissible and prone to causing an epidemic or pandemic within a local community, country, or globally. Viruses attach to and enter susceptible cells of a host, inside of which they can replicate and shed virus particles (virions) which infect additional cells and which can be spread to other organisms (e.g., through direct contact, contact between common environments, or through airborne transmission). Many viruses may be spread between different species, including between humans and various species of animal. Viruses can generally be categorized by genome type and include double-stranded DNA viruses (e.g., Adenoviridae, Papillomaviridae, Polyomaviridae, Herpesviridae and Poxviridae), partly double-stranded DNA viruses (e.g., Hepadnaviridae), single stranded DNA viruses (e.g., Parvoviridae), positive single-stranded RNA viruses (e.g., Astroviridae, Caliciviridae, Picornaviridae, Coronoviridae, Flaviviridae, Retroviridae and Togaviridae), negative single-stranded RNA viruses (e.g., Arenaviridae, Bunyaviridae, Filoviridae, Orthomyxoviridae, Paramyxoviridae, and Rhabdoviridae), and double stranded RNA viruses (e.g., Reoviridae). The infection of interest may be any infection compatible with the systems and methods described herein. In some embodiments, the infection of interest comprises any one of the infections disclosed elsewhere herein. In some embodiments, the infection of interest is a coronavirus (e.g., SARS-CoV-2 or MERS-CoV) infection, an influenza infection, an avian flu (i.e., bird flu) infection, a swine flu infection, an Ebola infection, a West Nile Virus infection, a Zika virus infection, a whooping cough infection, a mumps infection, a measles infection, an enterovirus infection, or other infection prone to causing an epidemic or pandemic.

In some particular embodiments, the infection of interest may be coronavirus infection. In more particular embodiments, the infection of interest may be a SARS-CoV-2 infection. Coronaviruses (CoVs) are RNA viruses belonging to the Coronaviridae family and can infect humans and other vertebrate animals. After the outbreak of severe acute respiratory syndrome (SARS) in the world in 2003, human coronaviruses (HCoVs) have been reported as pathogens that cause severe symptoms in respiratory tract infections. A new coronavirus SARS-CoV-2 (also known as SARS-CoV-02 or 2019-nCoV) originating in Wuhan, China in 2019 caused a global pandemic of acute respiratory syndrome. The disease caused by SARS-CoV-2 is called "coronavirus disease 2019" (COVID-19) by the World Health Organization (WHO). The WHO declared COVID-19 a global health emergency at the end of January 2020 and since then COVID-19 has caused large death tolls and the implementation of economic shut-downs, stay-at-home orders, quarantines, and other societal safety measures to curb the spread of COVID-19 in virtually every country across the globe. Common symptoms of SARS-CoV-2 include, but are not limited to fever, a dry cough, fatigue and difficulty breathing or shortness of breath. Some of these symptoms overlap with those of the flu, making detection difficult, but runny noses and stuffy sinuses are less common. The C.D.C. has also added chills, muscle pain, sore throat, headache and a new loss of the sense of taste or smell as symptoms to look out for. Most people fall ill around five to seven days after exposure, but symptoms may appear in as few as two days or as many as 14 days. Coronavirus particles contain four primary structural proteins, termed the spike (S), membrane (M), envelope (E), and nucleocapsid (N) proteins, all of which are encoded within the 3' end of the viral genome.

Testing for Infection of Interest

A subject may be tested for the presence of an infection of interest by subjecting a sample obtained from the subject to one or more assays for the infection of interest. As used herein, a sample may refer to processed (e.g., diluted) or unprocessed biological specimen collected from the subject. In various embodiments, the biological specimens may comprise nasopharyngeal secretions, oropharyngeal secretions, sputum, saliva, blood (e.g., whole blood, plasma, or serum), stool, urine, or other biologic material collected from or derived from the subject. Biological specimens may be collected by any standard means known in the art (e.g., swabs for collecting nasopharyngeal or oropharyngeal secretions). The assay may detect the presence of the pathogen (e.g., virus), pathogen-derived material, and/or pathogen-related biomarkers in the sample. For example, the assay may detect the presence of nucleic acids, proteins, human antibodies directed against the pathogen, or a combination thereof for the detection of the infection of interest (e.g., SAR-CoV-2). The signal of an assay may refer to the detectable signal (e.g., a fluorescence) that is detected and correlated to the presence of the pathogen, pathogen-derived material, or pathogen-related biomarker in the sample. The signal may be correlated to the amount of pathogen, pathogen-derived material, or pathogen-related biomarker in the sample. In some embodiments, the amount of pathogen, pathogen-derived material, or pathogen-related biomarker in the sample may be correlated to the amount of pathogen within a subject and/or the severity of infection within the subject. Depending on the infection, the amount of pathogen within a subject and/or the severity of infection within the subject may correlate to the time course of the infection or disease in the subject (e.g., how long ago the subject became infected) and/or how contagious the subject is likely to be.

In various embodiments, the assays may be configured as an RT-PCR test, a cartridge-based nucleic acid amplification test (CBNAAT), an antigen detection test, or an antibody test, each of which is well known in the art. Each type of test has its own advantages and disadvantages, including processing time, sensitivity (i.e., true positive rate), and specificity (true negative rate). Preferred sample types for RT-PCR, CBNAAT, and antigen detection tests may generally be nasopharyngeal or oropharyngeal secretions, whereas the preferred sample type for antibody tests are generally serological. Each type of test may provide more sensitive detection at different relative time courses of an infection. For example, at least for SARS-CoV-2, PCR-based tests may most sensitive during approximately the first one to two weeks of infection; antigen-based tests may be most sensitive during approximately the second and third weeks of infection; and antibody testing may be most sensitive after approximately three or four weeks since infection. Based on the different time frames over which the test types are most sensitive, PCR-based tests may be most suitable for identifying pre-symptomatic individuals. Antibody testing detects individuals who have already developed an immunity to the infection.

The type of test employed may impact the testing strategy. For example, a testing strategy which employs periodic mass testing of a population may employ a PCR-based test in order to more quickly identify and isolate infected individuals once infected, before they reach peak infectivity or to minimize the time they may come into contact with other members of the community during peak infectivity. Reverse transcription polymerase chain reaction (RT-PCR) is a methodology that can measure the amount of a specific viral RNA sequence in a sample to identify the presence of virus or viral material within a sample. RT-PCR is performed by reverse transcribing viral RNA into complementary DNA and then using polymerase chain reaction (PCR) to amplify specific DNA targets within the sample. Quantitative RT-PCR or qRT-PCR may be used to quantify the amount of target DNA or corresponding amount of viral DNA within a sample. The use of RT-PCR in clinical settings has been well established, but RT-PCR has not been readily adopted for rapid mass testing of populations (e.g., surveillance testing). Methods for performing RT-PCR are well known in the art. Other rapid-response technologies such as nanorods using lateral flow assays that can test a variety of samples like urine, blood, saliva, sweat, serum, and other fluids may also be employed.

Each assay may have a particular (lower) limit of detection (LOD), which may be defined as the lowest quantity of a substance (e.g., detected pathogenic biomarker) that can be distinguished by the assay from the absence of that substance (a blank control) with a given confidence level (e.g., 99%). By way of example, the FDA recommends that the LOD of an assay be determined by testing a dilution series of three replicates per concentration, and then confirming the final concentration with 20 replicates. Assays may have different effective LODs at different pool sizes of samples, as described elsewhere herein. Unless dictated otherwise by context, the LOD may be assumed to refer to the LOD for testing a single sample (i.e., a sample from one subject).

The ability for a particular assay to identify a subject as positive for the infection of interest may depend on the LOD of the assay and the amount of pathogen within the subject's biological specimen (e.g., viral load). The amount of pathogen within the biological specimen may depend on the individual subject as well as the timing of sample collection relative to the course of infection in an infected subject, which may be relatively dynamic over the course of infection, depending on the particular infection. SARS-CoV-2 infected individuals with varying severity of illness, have been detected to have viral load concentrations ranging from a few copies per mL up to or over $10^8$ copies/mL, with the interquartile range between $10^4$ to $10^6$ copies/mL as shown in the FIG. 1, reproduced from Zheng et al., BMJ. 2020 Apr. 21; 369:m1443 (doi: 10.1136/bmj.m1443), which is herein incorporated by reference in its entirety. It is possible for the range of viral titer in individual specimens to vary by six orders of magnitude.

As used herein, the term "assay" or "test" may refer to the components (e.g., reaction buffers, primers, etc.) needed to be combined with a sample, at least in its final processed form, to make a positive sample for a particular infection of interest detectable by means of a compatible testing modality. The assay may comprise one or more containers for containing the components. In some embodiments, at least one of the one or more containers may be configured for processing and/or detection by a testing modality (e.g., a thermocycler configured for RT-PCR or a cartridge configured for a CBNAAT). As used herein, testing "positive" for an infection of interest means that a sample has been determined to comprise an amount of a pathogen, pathogen-derived material, and/or pathogen-related biomarkers for the particular infection of interest which is at or above an assays' limit of detection (LOD). Testing "negative" for an infection of interest means that a sample has been determined to comprise an amount of a pathogen, pathogen-derived material, and/or pathogen-related biomarkers for the particular infection of interest which is not at or above an assays' limit of detection (LOD). A negative sample may comprise no pathogen, pathogen-derived material, and/or pathogen-related biomarkers or may comprise an amount that is below the LOD for the assay used. As will be understood by those skilled in the art, an assay may provide a level of "false negatives" and/or "false positives." A positive or negative status may be assigned to a pooled sample or to an individual sample. A positive or negative status may be assigned to an individual based on one or more tested samples. A positive assignment does not necessarily correspond to a clinical diagnosis of an infected individual, as would be performed by a health care practitioner, who may take other factors into consideration. A positive assignment may provide a probabilistic (e.g., a value within the range of 0 to 1) inference of infection in an individual or group of individuals. Positive test results may be deemed highly probably of infection. In various implementations, a positive assignment may result in a referral for an individual to a practitioner or facility capable of making a clinical diagnosis (e.g., a medical doctor may provide a note to a hospital for all highly probable cases). As used herein, a "test result" may comprise a positive or negative infection status for a tested sample (a pooled sample or individual sample). Optionally, the test result may comprise a value corresponding to the amount of pathogen, pathogen-derived material, or pathogen-related biomarker in a sample. For example, the units of detection may be correlated to an amount via a standard curve. The value may be represented in the same units as the LOD (e.g., counts/volume or counts/reaction). In various embodiments, the test results for one or more samples may be stored on memory (e.g., in a database). The test results may be associated on memory with unique subject identifiers (e.g., in a separate database).

In various embodiments, the LOD of an assay may be selected to provide an acceptable threshold of infection. An acceptable threshold of infection may be determined to be an amount of pathogen, pathogen-derived material, or pathogen-related biomarkers in an individual for which it is effective to assign the individual a negative infection status. In some instances, such individual may be presumed to provide a minimal risk of transmission of the infection of interest if present. For example, in some instances the level of infection may be low because it is early enough in the course of an infection that it will likely be detected on a future round of periodic testing enabling effective isolation. Such subsequent detection may still enable efficient isolation of the infected individual before the individual reaches peak infectivity and/or is able to extensively spread the infection within a population. In some instances, the level of infection may be low because an infected individual is near the end of the course of an infection and may be no longer contagious. In some embodiments, the mass testing scheme may be designed to allow a certain proportion of false negatives while still identifying a sufficient number of true positive individuals to allow effective control of the spread of the infection within a population.

The assays used by the methods and systems described herein may generally include any commercially-available assay for the infection of interest, including, for example, the specific SARS-CoV-2 assays disclosed herein. Examples of SARS-CoV-2 assays are listed in Table 1 below, reproduced from Tuzman, Biocentury. 2020 Apr. 1 (available at https://www.biocentury.com/article/304801/limits-of-detection-for-fda-authorized-covid-19-diagnostics), which is herein incorporated by reference in its entirety. Table 1 provides the Limit of Detection (LOD) of the first 22 manufacturers who submitted their assays for the FDA's Emergency Use Authorization (EUA) during the period from February to early April 2020 and are presented in order of increasing LOD, from 40 to 100,000 copies/mL (a 2,500-fold difference).

TABLE 1

Limit of Detection (LoD) of SarS-CoV-2 assays measured in copies per mL. LOD are reported as viral genomic sequence copies per volume are primarily reported in copies per mL; asterisks denote LODs originally reported as copies per µL.

| Company | Test | LOD | EUA date |
| --- | --- | --- | --- |
| Becton, Dickinson & Company | BioGX SARS-CoV-2 Reagents for BD MAX System | 40 copies/mL | Apr. 2, 2020 |
| Abbott | Abbott RealTime SARS-CoV-2 assay | 100 copies/mL | Mar. 18, 2020 |
| Abbott | ID NOW COVID-19 | 125 copies/mL | Mar. 27, 2020 |
| Quest Diagnostics | Quest SARS-CoV-2 rRT-PCR | 136 copies/mL | Mar. 17, 2020 |
| NeuMoDx | NeuMoDx SARS-CoV-2 Assay | 150 copies/mL | Mar. 30, 2020 |
| BGI Genomics | Real-Time Fluorescent RT-PCR Kit for Detecting SARS-2019-nCoV | 150 copies/mL | Mar. 26, 2020 |
| Cepheid | Xpert Xpress SARS-CoV-2 test (lab test) | 250 copies/mL | Mar. 20, 2020 |
| Cepheid | Xpert Xpress SARS-CoV-2 test (point of care test) | 250 copies/mL | Mar. 20, 2020 |
| bioMerieux | BioFire COVID-19 Test | 330 copies/mL | Mar. 23, 2020 |
| Primerdesign | Primerdesign Ltd COVID-19 genesig Real-Time PCR assay | 330 copies/mL* | Mar. 20, 2020 |
| Qiagen | QIAstat-Dx Resp. SARS-CoV-2 Panel | 500 copies/mL | Mar. 30, 2020 |
| DiaSorin | Simplexa COVID-19 Direct assay | 500 copies/mL | Mar. 19, 2020 |
| Quidel | Lyra SARS-CoV-2 Assay | 800 copies/mL* | Mar. 17, 2020 |
| Ipsum | COV-19 IDx Assay | 850 copies/mL* | Apr. 2, 2020 |
| CDC | CDC 2019-nCoV Real-Time RT-PCR Diagnostic Panel (CDC) | 3,160 copies/mL; 1,000 copies/mL* | Feb. 4, 2020 |
| ScienCell | ScienCell SARS-CoV-2 Coronavirus Real-Time RT-PCR Detection Kit | 3,160 copies/mL* | Apr. 3, 2020 |
| Co-Diagnostics | Logix Smart Coronavirus Disease 2019 (COVID-19) Kit | 4,290 copies/mL | Apr. 3, 2020 |
| Luminex | NxTAG CoV Extended Panel Assay | 5,000 copies/mL | Mar. 27, 2020 |
| LabCorp | COVID-19 RT-PCR Test | 6,250 copies/mL* | Mar. 16, 2020 |
| Avellino | AvellinoCoV2 test | 55,000 copies/mL* | Mar. 25, 2020 |
| Luminex | ARIES SARS-CoV-2 Assay | 75,000 copies/mL | Apr. 3, 2020 |
| GenMark | ePlex SARS-CoV-2 Test | 100,000 copies/mL | Mar. 19, 2020 |

Table 2, reproduced below from an application from QUEST DIAGNOSTICS™ to the FDA for Emergency Use Authorization (EUA) of its kit provides sensitivity data for the SARS-CoV-2 N1 and N3 genes. See, SARS-CoV-2 RNA, Qualitative Real-Time RT-PCR (Test Code 39433) Package Insert (available at https://www.fda.gov/media/136231/download). The LOD can be determined to be approximately 136 viral copies/mL (LOD 4 in Table 2). As expected, the assay functions with 100% detection rates at all higher LODs (sample IDs 1-3) for the N1 and N3 genes, at 95% and 100% detection rates for its own LOD of 136 copies/mL for the N1 and N3 genes, respectively, and finally at 81% and 86% detection rates for the lower LOD of 51 copies/mL (LOD 5) for the N1 and N3 genes, respectively. Samples with nCoV Ct<40.00 cycles were considered detected (positive) and samples with nCoV Ct>40.00 cycles were considered not detected (negative).

TABLE 2

Sensitivity results for nCoV RNA qualitative RT-PCR

| sample ID | nCoV copies/mL | nCov log copies/mL | nCoV N1 | | nCoV N3 | |
|---|---|---|---|---|---|---|
| | | | mean Ct | detection rate | mean Ct | detection rate |
| LOD 1 | 2,580 | 3.41 | 30.43 | 100% | 29.77 | 100% |
| LOD 2 | 968 | 2.99 | 31.95 | 100% | 31.02 | 100% |
| LOD 3 | 363 | 2.56 | 33.31 | 100% | 32.44 | 100% |
| LOD 4 | 136 | 2.13 | 34.88 | 95% | 34.27 | 100% |
| LOD 5 | 51 | 1.71 | 35.85 | 81% | 34.93 | 86% |

For comparison to assays approved for use in China and the EU, Table 3, reproduce from Wang et al., Clin Chem. 2020 Jul. 1; 66(7):977-979 (doi: 10.1093/clinchem/hvaa099), which is herein incorporated by reference in its entirety lists the six commercial kits that had been approved by NMPA (four having received CE marking (Liferiver, Huada, DAAN, and Sansure)) and various characteristics of the assays, including LODs. All six kits detected the viral RNA on the ABI 7500 Real-Time PCR System (THERMO FISHER SCIENTIFIC™).

TABLE 3

Characteristics and limits of detection of six approved SARS-CoV-2 RT-PCR kits

| Kits | Target Genes | RNA template volume (µL) | Each PCR reaction volume (µL) | SARS-COV-2 RNA with different concentrations (copies/mL) | | | | | |
|---|---|---|---|---|---|---|---|---|---|
| | | | | 7744 | 3872 | 1936 | 968 | 484 | 242 |
| Liferiver | ORF1ab/N/E | 5 | 25 | 100% | 100% | 100% | 100% | 100% | 90% |
| Huada | ORF1ab | 10 | 30 | 100% | 100% | 100% | 100% | 100% | 90% |
| GeneDx | ORF1ab/N | 2 | 20 | 100% | 70% | 50% | 35% | / | / |
| DAAN | ORF1ab/N | 5 | 25 | 100% | 100% | 100% | 100% | 100% | 35% |
| Sansure | ORF1ab/N | 10 | 40 | 100% | 100% | 100% | 100% | 100% | 90% |
| BioGerm | ORF1ab/N | 5 | 25 | 100% | 100% | 100% | 100% | 80% | 35% |

The LODs of currently approved SARS-CoV-2 assays can vary over 10,000-fold. Assays demonstrating a limit of detection (LOD) of approximately 100 copies of viral RNA per milliliter of transport media or less have generally been considered best-in-class assays. The higher the LOD of an assay, the higher the false negative rate that can be expected. An analysis of 27,500 test results for patients tested using the Abbott RealTime SARS-CoV-2 EUA assay suggested that each 10-fold increase in LOD is expected to increase the false negative rate by 13%, missing an additional one in eight infected patients. See, Arnaout et al., bioRxiv. 2020 Jun. 4; 2020.06.02.131144 (doi: 10.1101/2020.06.02.131144), which is herein incorporated by reference in its entirety. Based on this analysis, the highest LOD assays on the market can be expected to provide a false negative rate as high as 70%.

Population to be Tested

As used herein, the terms "subject," "member," "individual," or "patient" may refer to any mammalian organism from which a sample can be obtained to test for the presence of an infection of interest. The subject can be any mammal, such as a primate, cattle (cow or bull), horse, mouse, rat, dog, pig, goat, sheep, bat, rabbit, monkey, donkey, mule, buffalo, oxen, camel, etc. In some embodiments, the subject is a human. In some embodiments, the subject is a non-human mammal. For example, in some embodiments, the subject is a form of livestock. The subject may be any suitable age (e.g., infant, pediatric, adult). The subjects generally include symptomatic individuals, pre-symptomatic individuals, asymptomatic individuals, and/or individuals with immunity to an infection of interest unless otherwise specified. The terms "subject," "member," "individual," and "patient" may be used interchangeably herein unless dictated otherwise by context.

In various embodiments, the systems and methods described herein are configured for screening a population or community of individuals for the presence of an infection of interest. The terms "population" and "community" may be used interchangeably herein unless dictated otherwise by context. The testing may comprise testing of single individual samples and/or pooled samples, as described elsewhere herein. The testing may be used to identify the presence of an infection of interest in individual community members (i.e., be member-specific) and/or to determine the prevalence of the infection overall within a community (prevalence testing). The systems and methods described herein may be employed to test one or more populations.

Where a system or method is used to test multiple populations, the populations to be tested may be entirely distinct or may be overlapping (e.g., some individual members may belong to more than one population to be tested). The populations to be tested may be any grouping of individuals for which individual samples may be obtained. By way of example, populations to be tested may be defined by places of employment, schools or universities, health care facilities (e.g., hospitals), residential living facilities or communities (e.g., nursing homes or dormitories), political jurisdictions (e.g., precincts or counties), geographical communities, work unions, clubs or other social organizations, sports teams or leagues, a farm (e.g., for testing of livestock), etc. The size of each population to be tested may be of various sizes (e.g., from local to global). In some embodiments, a population to be tested comprises at least 10, 50, 100, 200, 300, 400, 500, 600, 700, 800, 900, 1000, 5,000, 10,000, 20,000, 30,000, 40,000, 50,000, 100,000 individual members. In specific embodiments, the population comprises at least about 1,000, 2000, 3000, 4,000, or 5,000 individual members (e.g., at least about 1,000). In some embodiments, a population to be tested comprises no more than 1000, 5,000, 20,000, 30,000, 40,000, 50,000, or 100,000 individual members. In some embodiments, the population is split up into at least about 100, 200, 300, 400, 500, 600, 700, 800, 900, 1,000, 2,000, 3,000, 4,000, 5,000, or 10,000 pools, as described elsewhere herein. In specific embodiments, the population to be tested comprises members of system-relevant professions such as doctors, nurses, heath care practitioners, police, firefighters, nursing home residents and/or employees, government administrators, teachers and staff of schools and universities, students, sanitation workers, grocery store or food service employees, retail employees, and other essential workforce members which may be at high risk of infection by the nature of their employment.

In some embodiments, a population to be tested is treated as a unit. For examples, samples for a particular population to be tested may be collected, shipped, sorted, processed, analyzed, and/or reported on, as described elsewhere herein, in a unitary or coordinated fashion. Each population to be tested (e.g., a population identifier and/or population characteristics, such as number of population members, identify of individual population members, estimated infection rate, etc.) may be stored on memory (e.g., in a database) of a system, as described elsewhere herein. Data for individual members of a population to be tested may be input to and/or transmitted from a central processor (e.g., a server) as a unit. In some embodiments, one or more administrators may be associated with a population to be tested. The one or more administrators may play roles in collecting samples, processing samples, shipping samples, collecting and/or providing information on individual population members, and/ or receiving information (e.g., test results). For example, the one or more administrators may comprise a human resources representative of a place of employment, a school nurse, or other administrative official of an organization. The one or more administrators may or may not be included as members of the population to be tested. In various embodiments, the population to be tested may only be a portion of a system or group of people described herein. For instance, one or more members of an organization may elect not to participate in the testing or may not be available for a particular round of testing.

Pooled Sample Testing

A population of individuals may be tested for an infection of interest according to a pooled sampling scheme. Pooled sampling comprises combining samples (whole samples or aliquots of samples) into a single pooled sample (i.e., composite sample) and testing the pooled sample for an infection of interest prior to deciding whether to test and subsequently testing any of the constituent samples of the pool (individual samples or smaller pools of individual samples) separately for the same infection of interest. As used herein, pooled "testing" refers to testing performed via pooled sampling, unless indicated otherwise by context. As used herein, reference to the size of a pool (e.g., a "smaller" pool or "larger" pool) will refer to the number of individual samples that are combined in the pool, unless otherwise dictated by context. For example, a pool combining samples from 32 individuals is larger than a pool combining samples from 16 individuals. As used herein, when a pool of samples is said to comprise, include, or consist of "individuals", it will be understood that the pool comprises, includes, or consists of, respectively, samples or aliquots of samples obtained from those individuals, unless dictated otherwise by context. Aspects of sample compositing, in general, are additionally provided in Rajagopal et al., Groundwater Monitoring & Remediation. 1989 March; 9(1):186-92 (doi.org/10.1111/j.1745-6592.1989.tb01130.x), which is herein incorporated by reference in its entirety.

A pooled sampling scheme may comprise a hierarchy of pools or groups. The hierarchy may comprise a tree-like structure (e.g., a decision-tree structure) in which each pool within the hierarchy extends via two or more branches either to a smaller pool of samples comprising a subset of the individuals within the pool (a "mini-pool") or to an individual sample within the pool. At the top of the hierarchy is a base pool (positioned at a level $S_0$) comprising a total number of individuals, N, making an N-sample or N-member pool. At the bottom of the hierarchy are a total of N non-pooled individual samples (level $S_f$, each consisting of 1 individual). The hierarchy may comprise one or more mini-pools between the base pool and the individual samples. Unless explicitly dictated otherwise, mini-pools are non-overlapping (individual members do not belong to more than one mini-pool at any level of the hierarchy). For example, the base pool may be divided into two smaller mini-pools (at level $S_1$). In certain embodiments, the individuals within each pool or mini-pool that is divided into a smaller mini-pool may be equally divided or substantially equally divided (e.g., if the number of individuals is not evenly divisible by the number of branches) among the smaller mini-pools. For example, the base pool $S_0$ may be divided into two mini-pools which may each have N/2 or approximately N/2 individuals (e.g., a whole number distribution of samples which is as close as possible to N/2). Similarly, each mini-pool at level $S_1$ may likewise be divided into two mini-pools at a lower level of the hierarchy, level $S_2$, such that each mini-pool at level $S_2$ comprises N/4 or approximately N/4 individuals and so forth. In some embodiments, the hierarchy may not comprise any mini-pools but only a base pool (at level $S_0$) and individuals at level ($S_1$).

The branching of mini-pools into smaller mini-pools may continue until the mini-pool is divided into individual samples. According to some embodiments, the hierarchy comprises a consistent branch number, B, such as 2, in which each pool or mini-pool within the hierarchy is divided into two smaller sized populations (e.g., mini-pools or individual samples). According to some embodiments, the branch number may be 3, 4, 5, 6, 7, 8, 9, 10, or more. According to some embodiments, the hierarchy comprises a consistent branch number, except that a mini-pool is not divided into mini-pools smaller than 4 individuals, particularly when B is 2, such that the individual samples, at level $S_i$, are positioned as the next lower level if the mini-pools would otherwise comprise less than 4 individuals. Testing of mini-pools smaller than 4 individuals (i.e., mini-pools of 3 or 2 individuals) generally requires the testing of at least 4 samples (one for each of at least two-mini-pools and one for at least each individual in a positive mini-pool) which in certain hierarchy schemes, particularly where the branch number B is 2, does not provide a reduction in test number compared to testing each of the individuals within a pool of 4 individuals separately. As will be understood in context, hierarchies comprising the pooling of 4 individuals at the level above $S_i$ may nonetheless be schematically represented by two branches extending from a pool or mini-pool each splitting into two additional branches that connect to the 4 individuals with the understanding that pooling/testing will not be performed at the nodes between the lowest level branches. Pooled sampling is also advantageous in that it provides a level of quality assurance by performing multiple rounds of testing on specimens at different levels of the hierarchy.

In some embodiments, particularly where a hierarchy employs a branch number, B, of 2, the base pool comprises a total number of individuals N set according to the formula $N=T^n$ (a binary framework), wherein n is any integer greater than or equal to 3. For example, N may be 8, 16, 32, 64, 128, 256, 512, 1028, etc. In some embodiments, the total number of levels in the hierarchy may be n, where there is a consistent branch number, B, of 2 such that the hierarchy comprises levels from $S_0$-$S_{n-1}$ (i.e., $S_i=S_{n-1}$). In some embodiments, the total number of levels in the hierarchy may be n-1, where there is a consistent branch number, B, of 2 except that 4 individuals (at level $S_i$) are grouped into mini-pools of 4 at the next highest level rather than mini-pools of 2, such that the hierarchy comprises levels from $S_0$-$S_{n-2}$ (i.e., $S_i=S_{n-2}$).

In some embodiments, a hierarchy may comprise a base pool comprising a total number of N individuals set according to the formula $N=B^n$, where B is the branch number and n is any integer greater than 2. Hierarchy schemes comprising $B^n$ total individuals with a consistent branch number of B (including where n=2) may be advantageous in that the individuals within a pool or mini-pool may be evenly distributed among the next lower level. In some embodiments, the total number of levels in the hierarchy may be n, where there is a consistent branch number, B, such that the hierarchy comprises levels from $S_0$-$S_{n-1}$ (i.e., $S_i=S_{n-1}$).

In other embodiments, the total number of individuals N may not be determined by the branch number B. In embodiments where the total number of individuals in a given pool or mini-pool is not evenly divisible amongst the next lowest mini-pool of samples, the individuals may be distributed amongst the mini-pools as evenly as possible. In some embodiments, the hierarchy does not use a consistent branching scheme, such that the number of branches between one level and the next lower level (e.g., between $S_0$ and $S_1$) may not be the same number of branches extending from that next lower level (e.g., between $S_1$ and $S_2$). In some embodiments, the number of branches extending downstream from a mini-pool at one level of the hierarchy may not be the same as the number of branches extending from another min-pool at the same level of the hierarchy, particularly where the mini-pools each comprise a different number of individuals.

In some embodiments, all members of a population to be tested are included in a single hierarchy structure. In some embodiments, only a portion of the members of a population to be tested are included in a single hierarchy. The members of a population to be tested may be divided into two or more hierarchies such that no single pool comprising samples of all the individual members is tested for the infection of interest. For example, the total number of members within a population to be tested may be greater than a maximum number of total individuals within a base pool, N, that can effectively be tested (e.g., without diluting the base pool sample beyond a limit set by the LOD of the assay being used). In some embodiments, an optimal base pool size is determined for a population (e.g., based, for example, at least in part on the estimated infection rate within that population). If the number of members in the population is greater than the optimal base pool size, the members may be distributed into a number of hierarchies comprising the optimal base pool size. If the number of members within the population to be tested is not evenly divisible into a number of pools of optimal base pool size, the residual members may be placed into their own hierarchy comprising a total number of individuals, N, less than the optimal base pool size or may be distributed into a plurality of hierarchies comprising base pool sizes that are smaller than the optimal base pool size. For instance, the residual members may be distributed into a plurality of hierarchies that maximizes the number of members who may be placed into a hierarchy comprising a total number of individuals, N, set by $N=B^n$, optionally, where B is 2. In some embodiments, single sample testing of individual samples may be performed on one or more residual members. In various embodiments, the population to be tested may be divided into at least, 10, 50, 100, 200, 300, 400, 500, 600, 700, 800, 900, or 1,000 hierarchies or base pools.

One or more sample may be collected for each individual in the population to be tested. In some embodiments, one primary sample is collected for each individual within a population to be tested. The primary sample may comprise a biological specimen as described elsewhere herein collected from the individual and diluted into a volume of buffer or media (e.g., a stabilizing buffer). A pooled sample may be prepared by removing an aliquot of the primary sample (after the sample has been sufficiently mixed or incubated with the dilution buffer) and combining it with aliquots from other individuals within the same pool to form a sufficient volume for testing. Additional buffer for diluting the pooled sample may or may not be added to the pooled aliquots. In some embodiments, the primary samples may be diluted to a final volume prior to removing any aliquots (e.g., a volume sufficient for testing after removal of all anticipated aliquots). In some embodiments, the primary samples may be only partially diluted (e.g., to a volume sufficient to remove the anticipated one or more aliquots) but may be further diluted before any testing is ultimately performed on the primary sample itself. In some embodiments, multiple aliquots may be removed from the primary sample before any testing has occurred. In some embodiments, aliquots may be removed from the primary sample as needed based on test results from a pool which included the individual corresponding to the primary sample. The primary sample may be diluted each time before an aliquot is removed. In some embodiments, multiple primary samples may be collected for each individual. One or more of the primary samples may be used to prepare pooled sample. At least one of the primary samples may be retained for potential testing of the individual alone. In some embodiments, multiple individual samples are prepared from a single specimen collection tool such as a swab. The collection tool may be sequentially incubated in different volumes of buffer to prepare multiple individual samples (e.g., without mixing). Pooled testing may be performed by using the earliest prepared samples at the highest levels of a hierarchy (e.g., the first prepared sample is used to prepare a sample for testing the base pool). Pooled testing may be performed by using the earliest prepared samples at the lowest levels of a hierarchy (e.g., the first prepared sample is retained for testing the individual alone if needed). Examples of methods for pooling samples for testing are provided in U.S. Pat. App. Pub. No. 2020/03474654 to Schmidt et al., published on Nov. 5, 2020, which is herein incorporated by reference in its entirety. Unless dictated otherwise by context, the pooling of samples may be performed according to any of the methods described therein, optionally including the use of any buffers or reagents described therein, wherein the infection of interest may be SARS-CoV-2 or another suitable infection. In various embodiments, the biological specimens may be collected into a protective buffer, such as DNA/RNA Shield™ (ZYMO RESEARCH™), which may stabilize nucleic acids in the sample (e.g., for a PCR-based assay) for several days (e.g., at least 50 days at room temperature). In various embodiments, the specimens may be collected directly into a container configured for performing the assay, such as a PCR-ready tube.

The members within a hierarchy may be tested for an infection of interest by first testing a base pool for the infection of interest. After a base pool has been tested, testing may move to the next lower level of the hierarchy. If the base pool tested negative, then no further samples may be tested, including individual samples. Individuals within the negative base pool may be presumed to be negative for the infection and assigned a negative status. If the base pool tested positive, then each of the populations (i.e., mini-pools or individuals) at the next lower level is tested. If a mini-pool is tested, the preparation of the pooled sample may be performed in substantially the same manner as described for the base pool. Differences in volume related to the total number of constituent samples may be accounted for, for example, at the aliquot stage and/or dilution stage. If a mini-pool tests negative, then no further testing may be performed for individuals within the negative mini-pool or for additional mini-pools positioned downstream of the negative mini-pool which comprise subsets of those individuals. Individuals within the negative mini-pool may be presumed to be negative for the infection and assigned a negative status. If a mini-pool tested positive, then each of the populations (i.e., mini-pools or individuals) at the next lower level is tested. The procedure may be repeated until each individual within the hierarchy is assigned a negative status via the negative result of a pooled sample upstream in the hierarchy or until the individual sample is tested alone. If the individual sample is tested alone, the individual is assigned either a positive or negative status for the infection of interest based on the test result for the individual.

The collection of samples and/or the preparation of samples for testing may be performed in accordance with the number of tests that may need to be performed for a predetermined hierarchy structure to identify each individual within the hierarchy as positive or negative for the infection of interest. For example, the volumes of the collected samples may be prepared such that there is sufficient volume to prepare the maximum number of pooled samples that may be needed. Likewise, the hierarchy may be designed such that the maximum number of tests that may be needed to identify each individual as positive or negative for the infection of interest does not exceed the sample collection capacity with an understanding that an assay used to perform one or more of the tests may limit the amount of sample dilution that is practical to effectively identify the sample as positive or negative, as described elsewhere herein.

Total Required Tests (TRT)

The number of tests that are required to identify each individual within a hierarchy as either positive or negative for an infection of interest is variable and depends on the proportion of the individuals within the hierarchy that are positive for the infection of interest as well as their relative positioning within the hierarchy. For a hierarchy which comprises one or more mini-pools, minimizing the number of tests that are needed to identify each individual within a hierarchy as either positive or negative can generally be achieved by positioning the positive individuals as closely as possible to each other at level $S_i$ of the tree structure (i.e., clustering the positive individuals together). Positioning positive individuals adjacent to one another in the hierarchy results in the positive individuals being confined to a minimal number of mini-pools as the tree structure is ascended and likewise the negative individuals being confined to a minimum number of mini-pools as the tree structure is ascended. In other words, it is more likely to make more of the mini-pools within the hierarchy homogenous (comprising all positive individuals or all negative individuals). Because additional testing will generally need to be performed on all downstream populations (mini-pools or individuals) at the next lower level of the hierarchy for a positive mini-pool regardless of whether only one constituent individual is positive or all the constituent individuals are positive, it is advantageous to include as many of the positive individuals as possible in the positive mini-pool. Doing so generally increases the number of mini-pools within a hierarchy that comprises no positive individuals (i.e., all negative individuals), such that no additional downstream testing will be needed for individuals within the negative mini-pools to identify them as negative. Likewise, having a lower total number of positive individuals within a given hierarchy structure of given base pool size, generally reduces the number of positive mini-pools and the number of additional downstream tests that are needed to identify each individual as positive or negative for the infection of interest.

Each hierarchy structure may comprise a minimum number of tests and a maximum number of tests required to identify the constituent members as positive or negative, for a given number of positive individuals. The minimum and maximum number of tests may define a solution space for the number of tests needed to identify the constituent members as positive or negative (i.e., the total required tests ("TRT")). In some instances (e.g., when all the constituent individuals or all but one of the constituent individuals are positive), the minimum and maximum number may be the same. In other instances, the maximum is greater than minimum, particularly at lower infection rates. In some instances, the number of tests needed may be a number between the minimum and maximum, depending on where in the hierarchy structure the positive individuals are positioned. The number of tests needed, or TRT, to definitively assign each individual within a hierarchy a positive or negative infection status can define a solution space of one, two, three, or more numbers. The solution space can be determined computationally for a given hierarchy structure and methods for doing so are well known in the art.

Figure 2A:
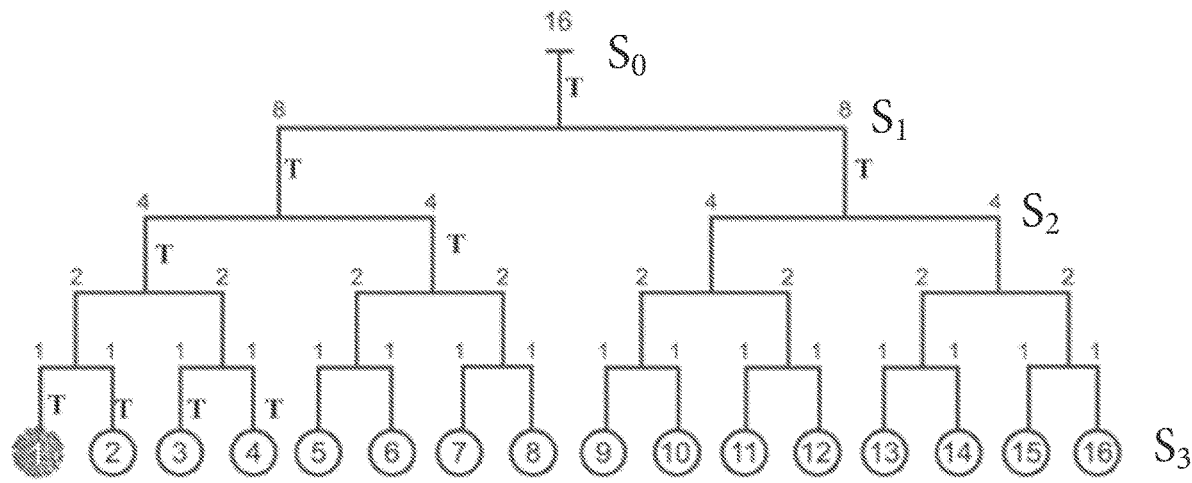
FIGS. 2A-2C schematically depict examples of different distributions of positive individuals for an infection within a pooled sample hierarchy used for performing member-specific testing on a group of 16 individuals. "T" indicates that the pool or individual will need to be tested for the specific distribution in order to complete the testing of the pool. Each hierarchy comprises an identical structure of one level individuals ($S_3$) downstream of three levels of sample pools ($S_0$-$S_2$).
Figure 2B:
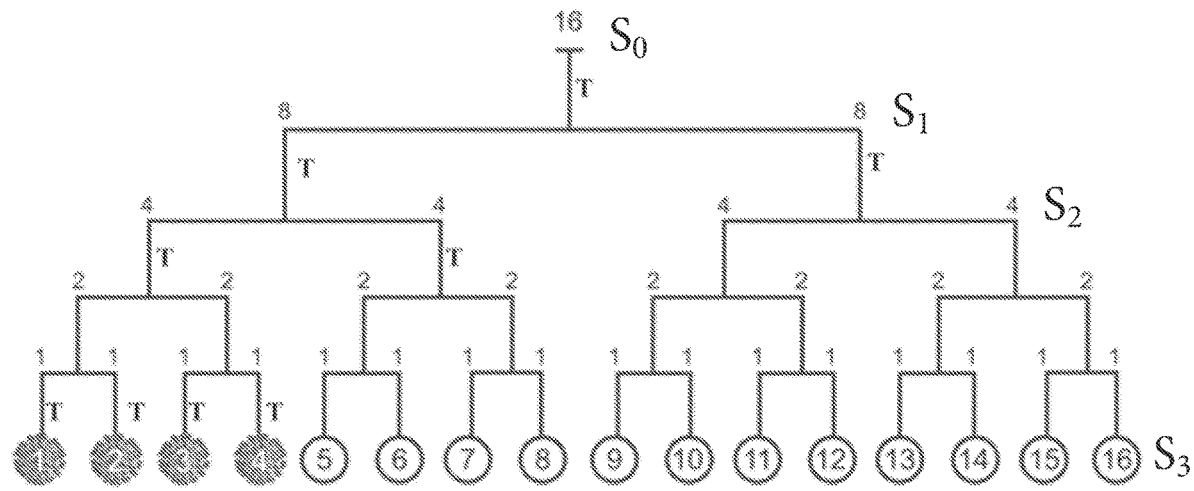
Figure 2C:
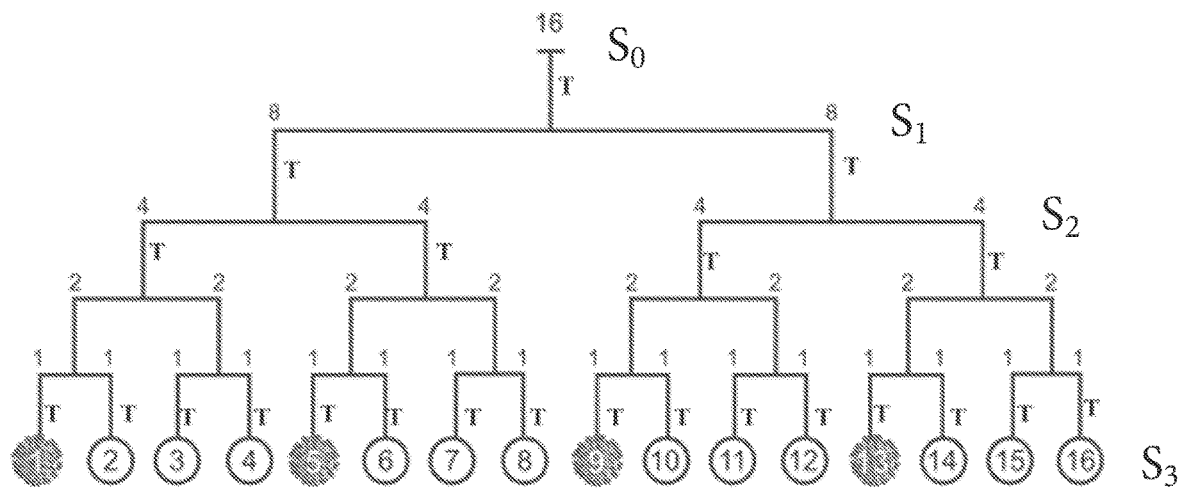

By way of example, FIGS. 2A-2C each schematically illustrate pooled sample hierarchies comprising 16-sample base pools (N=16) with a consistent branch number of 2

(B=2), except that the 4 mini-pools at level $S_2$ each comprise 4 effective branches extending directly to 4 individuals ($S_i=S_3$). The "T" symbol indicates the positions within the hierarchy where a test is required to identify the individuals as positive or negative according to a pooled sample testing scheme. In FIG. 2A, only one of the 16 individuals is positive (representative of an infection rate of 1/16 or 6.25%), indicated to be at position 1. Since, apriori, it is known that there is only one positive individual in the 16-member population, the test of 16-sample base pool must be positive, assuming an assay with a sufficient LOD is used. Furthermore, only one of the two downstream 8-sample mini-pools can be positive. Traveling even further down the tree, only one of the two 4-sample mini-pools downstream of the positive 8-sample mini-pool can be positive. Finally, all four individuals within the positive 4-sample mini-pool must be tested to conclusively identify the one positive individual and ensure that indeed only 1 of the 4 individuals is positive. Accordingly, the TRT is 9 regardless of where the one positive individual is positioned within the 16 available positions of the hierarchy. Thus, the solution space is simply 9 and 7 tests are saved when compared to testing each of the 16 individuals separately (single sample testing).

Figure 4:
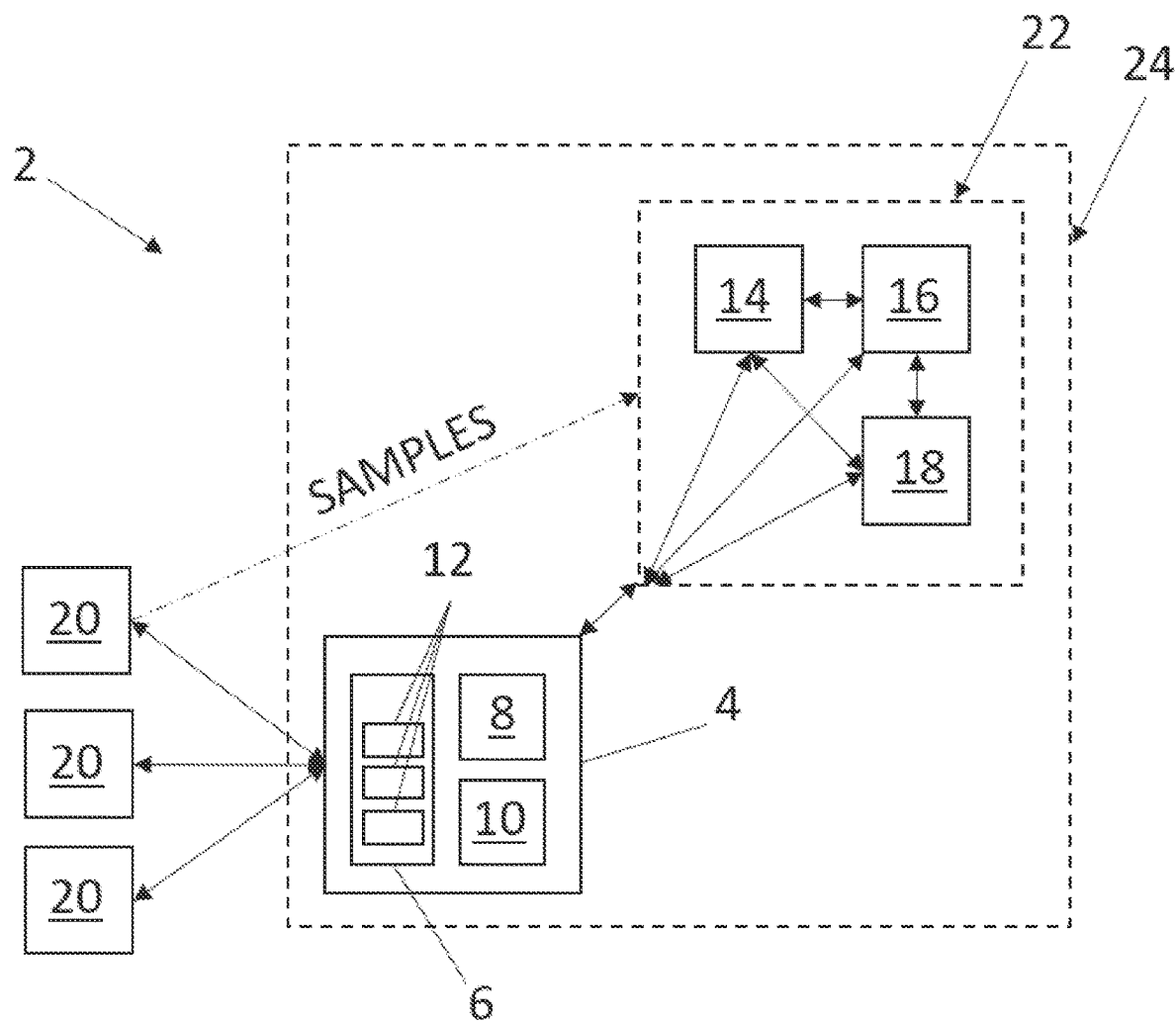
FIG. 4 schematically illustrates an example of a system for automating aspects of mass testing.

In the scenarios depicted by FIGS. 2B and 2C, 4 of the 16 individuals are positive (representative of an infection rate of 1/4 or 25%). In FIG. 2B, the 4 positive individuals are indicated to be at positions 1, 2, 3, and 4, which is a best-case scenario for this particular hierarchy structure and infection rate, as the TRT is 9 and 7 tests are saved when compared to testing each of the 16 individuals separately. Thus, in the best-case scenario, no additional tests are needed to identify the three additional positive individuals relative to the scenario illustrated in FIG. 2A, where only one individual is positive. In FIG. 2C, the 4 positive individuals are indicated to be at positions 1, 5, 9, and 13, which is a worst-case scenario for this particular hierarchy structure and infection rate, as the TRT is 23 and 7 tests are wasted when compared to testing each of the 16 individuals separately. As seen in FIG. 2C, the 4 positive individuals are dispersed such that every upstream mini-pool will comprise at least positive individual.

In some embodiments, pooled sample testing schemes which comprise hierarchies having base pools but no mini-pools are evaluated. In such testing schemes, the TRT solution space for each hierarchy will be 1 (for a negative pool) or N+1 (for a positive pool). Where the population to be tested is larger than the size of the base pool, N, the solution space becomes more complicated, as the distribution of positive individuals within a plurality of hierarchies/pools will resemble the distribution of positive individuals within a plurality of mini-pools in a single hierarchy comprising mini-pools. The larger the total population, the larger the total solution space for the population becomes. The same principles discussed with respect to characterizing the TRT solution space of a single hierarchy comprising mini-pools may be applied. For example, the plurality of base pools may be evaluated as if they were each mini-pools of a single larger pseudo-base pool, although it will be understood that no samples will be pooled to construct the pseudo-base pool and no test will be conducted for the pseudo-base pool. Similarly, for pooled testing schemes comprising hierarchies having mini-pools, the cumulative TRT solution space (or solution space for total TRT) for a population may be characterized, accounting for possible variations in the distribution of positive individuals across various pools. The size of the base pools may influence the cumulative TRT solution space for the population to be tested.

In some instances, the TRT may be less than the total number of individuals, N, such that the pooled sample testing scheme reduces the number of tests needed to identify each individual as positive or negative when compared to single sample testing at the outset (i.e., saves tests). In some instances, the TRT may be the same as the total number of individuals, N. In some instance, the TRT may be more than the total number of individuals, N, such that the pooled sample testing scheme is less efficient at identifying each individual as positive or negative when compared to single sample testing from the outset (i.e., wastes tests). According to certain embodiments, methods for testing individuals within a population of interest comprise determining the solution space for one or more hierarchy structures given one or more potential numbers of positive individuals. The one or more potential numbers of positive individuals within the population may be determined according to an estimated infection rate within the population, as described elsewhere herein. Given the calculated solution space, a probability of having a TRT less than N (i.e., reducing the number of tests needed by employing the pooled testing scheme) may be determined and/or a probability of having a TRT greater than N (i.e., increasing the number of tests needed by employing the pooled testing scheme) may be determined (e.g., given a random distribution of the positive individuals or some other distribution). In some embodiments, the probability of increasing or decreasing the number of tests needed by a certain integer (e.g., for each integer difference possible based on the solution space for the TRT) when compared to testing each individual separately are determined (i.e., the probability of saving or wasting a certain integer number of tests or at least a certain integer number of tests). In some embodiments, an average number of tests saved or wasted is determined based on the probability distribution over the solution space. The average may be weighted or not-weighted by the number of tests saved/wasted. In specific embodiments, an estimated TRT is determined from a simulation, such as one of the simulations described elsewhere herein. The use of a simulator may effectively account for the impact of differences in probability between different TRTs within the solution space over a large number of individuals (large number of pools) without having to mathematically characterize probabilities of TRTs within large solution spaces. In various embodiments, the specific testing scheme employed (e.g., the specific pooled sample testing scheme) may be determined based on a comparison of the simulated TRT (e.g., an average TRT from multiple runs of a simulation) for a plurality of testing schemes. The testing schemes may comprise single sample testing and/or multiple pooled sample testing schemes (e.g., different base pool sizes).

According to certain embodiments, methods for testing individuals within a population of interest comprise generating, displaying, and/or accessing one or more taxonomy tables which characterize the solution space for the TRT. The taxonomy tables may comprise a minimum number and/or maximum number of TRT for one or more pooled sampling schemes. The taxonomy tables may comprise each potential TRT within the solution space for one or more pooled sampling schemes. The taxonomy tables may comprise an average TRT. For example, the taxonomy table may comprise an average TRT generated from a simulation, as described elsewhere herein. The taxonomy tables may comprise one or more measures of expected error, such as standard error, standard deviation, and/or confidence intervals. The taxonomy tables may comprise any one or more of the probabilities (e.g., as a percentage) associated with achieving a specific TRT or threshold TRT, as described elsewhere herein. The taxonomy tables may characterize the solution space for one or more given numbers of positive individuals and/or corresponding approximated infection rates (i.e., the number of positive individuals in a pool divided by the pool size).

In some embodiments, the solution space may be characterized for each possible number of positive individuals within a hierarchy (e.g., from 0 or 1 individuals to 64 individuals for a hierarchy comprising a 64-member base pool). In some embodiments, the taxonomy table may characterize the solution space for each number of individuals (e.g., from 0 or 1) up to a predetermined approximated infection rate (e.g., about 1%, 5%, 10%, 15%, 20%, 21%, 22%, 23%, 24%, 25%, 26%, 27%, 28%, 29%, 30% or more) and/or may characterize the solution space for representative infection rates (e.g., 0.001%, 0.002%, 0.003%, 0.004%, 0.005%, 0.006%, 0.0007%, 0.008%, 0.009%, 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 2%, 3%, 4%, 5%, 10%, 15%, 20%, and 25%). In various embodiments, the solution space may be evaluated for infection rates between about 0.001% and about 5%. In some embodiments, the taxonomy table characterizes the solution space for different base pool sizes. For example, the taxonomy table may characterize the solution space for all pool sizes of $N=2^n$ for increasing integers of n, beginning at n=2 or 3, inclusive of all base pool sizes that are smaller than or equal to the size of the population to be tested. For example, the taxonomy table may characterize the solution space for a base pool size, N, of 4, 8, 16, 32, 64, and/or 128 individuals for a population of 128-255 individuals. In some embodiments, the taxonomy table may include at least one pool size that is larger than the population to be tested, particularly if the population is larger than the next smallest pool size, with the understanding that a sample pooling scheme could be used that resembles the scheme of the larger base pool size, but having the pool and at least some of the mini-pools comprising less than the ordinary number of individuals that would be expected. The ordinary number is defined as the size of the base pool comprising a number of individuals that can be distributed evenly across all mini-pools in the hierarchy. In some embodiments, the taxonomy table may also provide the solution space for testing each individual separately, where TRT=N (i.e., equivalent to a pool of $B^0$ or 1).

FIGS. 3A-3E represent examples of taxonomy tables for an $N=2^n$ hierarchy structure with a consistent branch number of 2 (B=2), except that the 4 mini-pools at the second lowest level each extend directly via 4 branches to 4 individuals (as in FIGS. 2A-2C). The taxonomy tables provide a TRT solution space defined by a range between a minimum and maximum number of TRT (or simply 1 TRT if the solution space is only 1 number). FIGS. 3A-3E provide illustrative taxonomy tables for 8, 16, 32, 64, and 128 samples/individuals, respectively. Each taxonomy table includes columns characterizing the solution space for single sample testing (equivalent to a pool of $2^0=1$) and $N=2^n$ pooled sample hierarchies, beginning at n=2 and continuing up to n=3, 4, 5, 6, or 7 respectively, for FIGS. 3A-3E, wherein the total number of individuals in the tested population are assumed to be evenly distributed into the multiple hierarchies when the base pool size is smaller than the total number of individuals in the population. Each taxonomy table includes rows characterizing the solution space for each number of potentially positive individuals from 0 up to the number corresponding to a 25% infection rate and the approximated infection rate for each row. Using these tables, the solution spaces for various potential $N=2^n$ sample pooling schemes can be compared to each other as well as to a single sample testing scheme. For instance, it can be seen from FIG. 3A that if only one individual within 16 individuals is positive, then it is more efficient to split the individuals up into hierarchies comprising two 8-sample base pools or four 4-sample base pools rather than combining all the samples into a single 16-sample base pool or performing single sample testing on all 16 individuals.

In some embodiments, one or more taxonomy tables may be part of a system for performing a method described herein. The one or more taxonomy tables may be stored on a memory (e.g., as part of a database). The one or more taxonomy tables may be accessed by a user and/or automatically accessed by a program implementing a method described herein. In some embodiments, one or more specific tables and/or specific values from the taxonomy tables may be accessed, displayed, and/or generated as part of a method described herein. The system may access one or more values from one or more taxonomy tables as circumscribed by one or more parameters, such as a number of positive individuals, an infection rate, a population to be tested size, a base pool size (N), a branch number (B), a TRT (e.g., all solution spaces encompassing TRTs below a threshold), a number of tests expected to be saved (e.g., all solution spaces encompassing TRTs that save at least a threshold number of tests), a probability (e.g., all solution spaces encompassing TRTs with probabilities of saving tests above a threshold), a particular assay, a limit of detection (LOD) for an assay, etc. In some embodiments, the one or more parameters is input by a user. For example, a user or a system may access the stored tables and return values from the tables for all $N=2^n$ solution spaces, optionally where n is greater than or equal to 4, that provide N-sample pool sizes smaller than a provided population size. Optionally, the returned solution spaces may be limited to solution spaces for a provided infection rate. The system may return the solution space for the closest approximated infection rate (based on the number of positive individuals divided by the base pool size), the solution spaces having approximated infection rates that are bound (above and below) by the provided infection rate, or all solution spaces within a predetermined margin of error from the provided infection rate (e.g., both above and below the provided infection rate or only above the provided infection rate). The taxonomy tables may be used to facilitate a user in determining the best (e.g., most efficient) testing scheme or may be used by a system to automatically determine the optimal testing scheme according to predetermined parameters (e.g., the system may determine the optimal base pool size, and optionally the best hierarchy structure). In various embodiments, the estimated infection rate may be presumed to have a 1%, 2%, 3%, 4%, 5%, 10%, 15%, or 20% margin of error.

One or more measures may be used to make decisions about the optimal (e.g., most efficient) testing scheme, such as whether to conduct single sample testing or pooled-sample testing and/or what is the optimal base-pool size for pooled sample testing. In some embodiments, testing decisions may be made according to the minimum TRT for a given solution space. In some embodiments, testing decisions may be made according to the maximum TRT for a solution space. In some embodiments, testing decisions may be made according to an average TRT for the solution space, as described elsewhere herein.

Device Insights

As discussed elsewhere herein, the LOD for a given assay may place an effective upper limit on the size of a base pool. The sensitivity, resolution, errors, false positives and false negatives, and the ultimate performance of the assays used may vary as a function of sizes used for pooled sampling (pool sizes). The limitations placed on a pooled sample testing scheme by an assay's sensitivity and/or analytical resolution (e.g., LOD) may be referred to as "device insights," as the values provide insight into the size of pools that may be used to effectively assign individuals in a population a positive or negative infection status. The device insights may, for example, help determine the appropriate column (position on the x-axis) for defining a TRT solution space in FIGS. 3A-3E. The solution space of TRTs may be a function of device insights, such as the LOD, of one or more assays. A particular assay may not be able to reliably detect an infection below, for example, a threshold concentration set by the LOD (e.g., counts/volume). As described elsewhere herein, a testing strategy may comprise an acceptable threshold of infection (which may be expressed in the same units as the LOD, e.g., counts/volume) below which it is acceptable that an individual be identified as negative. The testing scheme may use a maximum hierarchy (base pools size) which retains the ability to identify a positive individual within the pool when the constituent samples are combined (diluting the sample of the positive individual). The acceptable threshold of infection can be used to determine a maximum pool size, since larger thresholds of infection will generally allow for larger pool sizes. The acceptable threshold of infection may be determined epidemiologically to contain spread of the contagion within the community (e.g., to keep the infection rate within a community below a certain level or to cause the infection rate to decrease).

The LOD for a given assay at a particular pool size may generally be inversely proportional to the pool size. Thus, the LODs at different pool sizes may be set according to the formula:

$$PS(1) \times LOD(1) = PS(2) \times LOD(2) \quad \text{Formula I}$$

wherein PS(1) represents a first pool size, LOD(1) represents the LOD at the first pool size, PS(2) represents a second pool size, and LOD(2) represents the LOD at the second pool size. The reported LOD for a particular assay (e.g., as reported by a manufacturer) for use in single sample testing (i.e., PS=1) may be used to calculate the expected LOD at various other pool sizes.

In some embodiments, a conservative approach to pooled sample testing may be employed wherein a base pool size does not reach or exceed a size in which a positive base pool comprising a single positive individual at the acceptable threshold of infection and a remainder of individuals with effectively no signal/counts (e.g., non-infected individuals) is undetectable (i.e., the positive signal from the one positive individual is diluted to a level below the LOD of the assay used to test the base pool). In other embodiments, an estimated infection rate may be used to determine the estimated number of positive individuals within a prospective base pool and the same logic may be applied. That is, the positive signal from the estimated number of positive individuals cannot be diluted to a level below the LOD of the assay used to test the base pool, assuming that each of the positive individuals is at the acceptable threshold of infection. Still, in further embodiments, not only the estimated number of positive individuals but also an estimated distribution of infection levels may be used to estimate the level of infection signal (e.g., total counts/volume) in the combined base pool. That is, the positive signal from the estimated number of positive individuals cannot be diluted to a level below the LOD of the assay used to test the base pool, assuming that the positive individuals comprise a predetermined distribution of infection levels. The predetermined distribution may resemble a reported distribution (e.g., from literature), a simulated distribution (e.g., specifically for the population being tested, as described elsewhere herein), or other estimate of the distribution within the population to be tested. The predetermined distribution may resemble a distribution within the population to be tested as a whole or may account for the specific distribution of member-specific traits within the population to be tested that are likely to have a correlation to infection levels within the population to be tested.

In various embodiments, the methods or systems described herein may use an estimated or assumed (e.g., a conservative) distribution of infection within a given base pool size to determine what size base pools can be effectively tested with one or more given assays having particular LODs. For example, a simulator may be used to simulate the distribution of infected individuals into various pool sizes as described elsewhere herein. The simulator may replicate one or more levels of infection (e.g., one or more bins of viral loads). The simulator can be used to determine the signal for each simulated pooled sample and make a call on whether or not a sample is correctly identified as positive/negative. The simulator may assume a binary 0% or 100% capture rate based on the input LOD or may simulate probabilistic determinations. The sensitivity or false negative rate over a large number of simulated tests may be used to select the testing scheme (e.g., maximum pool size). For instance, the false negative rate may be used to determine if the infection rate is likely to increase, decrease, or remain stable within a population. An acceptable false negative rate may be used to determine the appropriate testing scheme where applicable to any of the methods described herein.

In some embodiments, a maximum base pool size, $N_{max}$, may be set as a function of an assay's LOD. In some embodiments, $N_{max}$ can be about 10,000/LOD. In some embodiments, $N_{max}$ can be about 5,000/LOD. In some embodiments, $N_{max}$ can be between about 5,000/LOD and about 10,000/LOD. For example, $N_{max}$ can be about 5,500/LOD; 6,000/LOD; 6,500/LOD; 7,000/LOD; 7,500/LOD; 8,000/LOD; 8,500/LOD; 9,000/LOD; or 9,500/LOD. The $N_{max}$ may depend on the estimated infection rate within the population to be tested. The $N_{max}$ may be increased by employing population member sorting as described elsewhere herein. The $N_{max}$ may be higher for a higher acceptable threshold of infection. The $N_{max}$ may be higher for a higher allowance rate of false negatives within a population to be tested. The $N_{max}$ may depend on the overall testing strategy, such as the frequency of testing and/or an acceptable level of infection within the population to be tested. For example, the $N_{max}$ may be higher for a population that is tested via pooled sampling weekly compared to a population that is tested via pooled sampling monthly. Similarly, the $N_{max}$ may be higher for a testing strategy that includes periodic testing of individuals (single sample testing) compared to a testing strategy that does not. The $N_{max}$ may be higher for testing strategies that comprises more frequent single sample testing (e.g., weekly vs. monthly). In various embodiments, the testing strategy may be designed to quickly achieve as low an infection rate as possible within a population and then containing the infection rate at that level (e.g., long term or until the contagion is extinguished from the population). In such implementations, the $N_{max}$ may be relatively lower during the first round (or first few rounds) of surveillance testing to attain a more accurate identification of positive individuals and better contain the contagion in the short-term, reducing the spread and lowering the infection rate. Once a low infection rate within the community is attained, the $N_{max}$ may be higher (e.g., for long-term surveillance) at a level configured to maintain the infection rate at its reduced level.

For a hierarchy structure comprising mini-pools, the LOD of the assay used to test the base pool or another upstream mini-pool may be assumed to sufficient for the mini-pool to be tested. In some embodiments, particularly where assumptions were made about a distribution within the population to be tested, the maximal pool size may be independently calculated for one or more mini-pools (e.g., all mini-pools) within a hierarchy before an appropriate base pool size and/or hierarchy structure is selected. In some embodiments, the same assay is used to perform all tests within a hierarchy structure. In some embodiments, assays having different (e.g., higher) LODs than the assay used to test the base pool or an upstream mini-pool may be used to test a downstream mini-pool. The assay (e.g., LOD) suitable for a particular mini-pool may be selected based on the size of the mini-pool and/or predicted distribution within the mini-pool. One or more suitable assays or LODs may be determined from one or more taxonomy tables as described elsewhere herein. In some implementations, the mini-pool may be assumed to be the base-pool in one or more of the taxonomy tables. As higher quality assays (e.g., assays with a lower LOD) may cost more than lower quality assays, a hierarchy that uses different assays (e.g., assays having different LODs) depending on the size of the pool to be tested may save total costs on the TRT.

Community Insights

The solution space for the TRT characterizes the TRTs for all possible positions of a given number of positive individuals within a hierarchy of a given base pool size, N. If members of the population to be tested are randomly distributed within the hierarchy, the expected TRT or most likely TRT (e.g., an average TRT) may be expected to depend on the number of times a TRT value occurs among the cumulative scenarios considered when determining a solution space. Disclosed herein are methods for shifting the expected TRT towards the minimum TRT within a solution space.

As described elsewhere herein, the minimum TRT for a given hierarchy is expected to occur when positive individuals are clustered closely together within a given hierarchy structure. For example, a hierarchy comprising a base pool of 16 individuals may comprise 16 positions or locations within the hierarchy where each of the 16 individuals is assigned. These may be referred to herein as positions 1 through 16. For a 16-member base pool having 4 positive individuals, the best-case scenario in terms of achieving the minimum TRT, as demonstrated in FIG. 2B, is when the 4 positive individuals are positioned at positions 1-4, positions 5-8, positions 9-12, or positions 13-16, since these groupings ensure all the positive individuals are in the same mini-pool at the next highest level.

In order to increase the likelihood of positioning positive individuals in a population to be tested within positions that are expected to minimize the TRT, a relative probability of infection may be assigned to one or more members of the population to be tested. In some embodiments, a relative probability of infection is assigned to at least 2, 3, 4, 5, 6, 7, 8 or more members of a population to be tested. In some embodiments, a relative probability of infection may be assigned to at least 1 out of every 2, 4, 8, or 16 members of a population to be tested. In some embodiments, a relative probability of infection is assigned to each member of a population to be tested. In some embodiments, a relative probability of infection is assigned to each member of a population to be tested in which sufficient information is available for calculating a relative probability. In some instances, when sufficient information is not available for one or more members of a population to be tested to calculate a relative probability of infection, those members may be presumed to have an average relative probability of infection, a median relative probability of infection, a relative probability of infection equal to the highest calculated relative probability of infection, a relative probability of infection higher than the highest calculated relative probability of infection (e.g., a maximum probability of infection such as 1), a relative probability of infection equal to the lowest calculated relative probability of infection, or a relative probability of infection less than the lowest calculated relative probability of infection (e.g., a minimum probability of infection such as 0), with respect to the base pool which the individual is assigned or with respect to the population to be tested as a whole.

In some embodiments, each member of a base pool and/or a larger population to be tested are ranked or sorted (e.g., into an ordered list) based on the member's assigned relative probability of infection. The members may be sorted from highest to lowest relative probability or from lowest to highest relative probability. In some embodiments, the positions within a hierarchy structure are assigned according to the member's ranking. For example, in a 16-member base pool, the member with the highest relative probability of infection may be assigned to position 1, the member with the second highest relative probability of infection may be assigned to position 2, and so forth, until the member with the lowest relative probability of infection is assigned to position 16. Alternatively, the member with the lowest relative probability of infection may be assigned to position 1, the member with the second lowest relative probability of infection may be assigned to position 2, and so forth, until the member with the highest relative probability of infection is assigned to position 16. If one or more members share the same relative probability of infection, their positioning relative to one another may be random or based on an otherwise arbitrary factor (e.g., alphabetical order, sample ID #, etc.). Sorting the members of the population to be tested within the hierarchy according to their relative probability of infection can optimize the likelihood of achieving a lower TRT than if the members were not sorted (e.g., randomly distributed). In some embodiments, where the members of a population to be tested are divided into multiple hierarchies, the members with the highest relative probability and/or lowest relative probability may be clustered into as few hierarchies as possible. For example, the members may be sorted as described above, with the 16 individuals having the highest relative probabilities being sorted in a first 16-member hierarchy, the 16 individuals with the next highest relative probabilities being sorted into a second 16-member hierarchy, and so on.

In some embodiments, a relative probability of infection for one or more members of a population to be tested, may be determined by a statistical model. The statistical model may be a mixed variable statistical model. A mixed variable statistical model may be used to determine a sample location index (SLI) of the member which can be used to determine the appropriate location of the member within the hierarchy structure. The SLI may be representative of the relative probability of infection, with higher SLI values indicating a higher relative probability. In some embodiments, the SLI may be calculated according to Formula II:

$$SLI_i = \frac{\sum_{j=1}^{m} f_{ij} w_j}{\sum_{j=1}^{m} w_j}, \quad \text{Formula II}$$

wherein i=1 . . . n, representing the n individual members to be ranked; j=1 . . . m, representing m weighted factors; $f_{ij}$ represents a reported value for member i as relates to factor j; and $w_j$=the estimated weight assigned to factor j (e.g., Iv, may be between 0-1, 0-10, or 0-100, etc.). The values for factors $f_{ij}$ may represent nominal, categorical, ordinal, discrete, and/or continuous variables. In some embodiments, the $SLI_i$ may be more specifically represented by Formula III, for different types of factors f:

$$SLI_i = \frac{\sum_{j=1}^{m} x_{ij} y_{ij} z_{ij} w_j}{\sum_{j=1}^{m} w_j} \quad \text{Formula III}$$

wherein $x_{ij}$=0 or 1 (representing the value for member i as relates to factor j when the value for factor j can be provided as a yes/no answer); $y_{ij}$=1, 2, or 3 (representing the value for member i as relates to factor j when the value for factor j can be provided as a categorical answer such as small/medium/large, low/medium/high, ordinal ranking, or equivalent type of answer); and $z_{ij}$=any real number (representing the value for member i as relates to factor j when the value for factor j can be any continuous or discrete variable).

In some embodiments, values for $y_{ij}$ and/or $z_{ij}$ may be scaled or normalized. For instance, the values may be normalized against a normal or baseline value (e.g., from literature) or against the largest reported value for any member i within the sorted population (e.g., such that the values range from 0 to 1 or −1 to 1). In some instances, the z values may be positive only for a factor, wherein larger positive values are indicative of a higher probability of infection. In some instances, the z values may be negative only for a factor, wherein more negative values are indicative of a lower probability of infection. In some instances, the z values may be positive or negative for a factor. In various embodiments, the SLI formula may comprise only x factors, only y factors, only z factors, only x and y factors, only x and z factors, only y and z factors, or all of x, y, and z factors. In some instances, when sufficient information is not available for one or more members of a population to be tested for a specific factor and/or where the factor is not applicable, those members may be presumed to have an average value, a median value, a value equal to the highest calculated value, a value higher than the highest calculated value (e.g., a maximum value), a value equal to the lowest calculated value, or a value less than the lowest calculated value (e.g., a minimum value), with respect to the base pool which the individual is assigned or with respect to the population to be tested as a whole. In some instances, when sufficient information is not available for one or more members of a population to be tested for a specific factor and/or where the factor is not applicable, the weight, $w_j$, may be set to 0 for that specific individual, effectively removing the factor from the individual's SLI calculation.

The weights, $w_j$, for each factor j may be derived from and/or adjusted according to various sources. The weights may be derived from literature. The weights may be derived from independent experimentation. The weights may be optimized based on feedback from a system described herein. For example, a system may store test results (e.g., positive/negative) for each member in a tested population on a memory (e.g., in a database). The system may compare the test results for a population of individuals to the various corresponding factor values provided for those individuals (e.g., the factor values that were used to sort that population of individuals during the round of testing that produced the test results) and adjust the weighting of the factors such that the adjusted SLI provides an optimal correlation to the individuals who actually tested positive. Each round of testing should provide significant additional data to strengthen the statistical models employed. The system may use test results and/or factor values from multiple rounds of testing as data (e.g., training data or validation data). In some embodiments, the system optimizes the factors for a specific population to be tested based on previous test results and corresponding previously provided factor values confined to that that population. In some embodiments, the system optimizes the factors for a specific population to be tested based on previous test results and corresponding previously provided factor values for other previously tested populations, which may or may not include the population to be tested or members from the population to be tested. In some embodiments, the system may use a machine learning algorithm as is known in the art to optimize the weights, using the previous test results and corresponding factor values as data sets for training a model and/or validating a model which determines the weights. Any suitable feedback mechanism may be employed. Various specific methods of using data as feedback are well known by those skilled in the art. The feedback mechanism may be formed as part of a software engine.

The weighted factors may comprise individual-specific factors in which a value is independently assigned for the factor for each individual for which an SLI is calculated. In various embodiments, the weighted factors for calculating an SLI may generally be categorized as personal health factors (e.g., age, gender, existence of a preexisting condition, weight and/or BMI, blood pressure, cholesterol, resting heart rate, etc.), factors related to disease symptoms such as specific symptoms of the infection of interest (e.g., temperature, existence of fever and/or chills, cough, respiratory difficulty, body aches, headaches, loss of taste or smell, fatigue, sore throat, congestion, nausea and/or vomiting, diarrhea), personal habits or exposure risk (e.g., frequency of face-covering, social distancing, exercise, exposure to high-risk events, exposure to high-risk individuals, work environment, geographic location of residence and/or work, etc.), or demographic information (e.g., socio-economic status or income, race, religion, political affiliation, type of profession, etc.). The categories may or may not be mutually exclusive.

The estimated infection rate for a population to be tested and collection of factor values for a population to be tested may be referred to as "population insights" or "community insights," as the values provide insight into the likely distribution of an infection within a particular community or population. The community insights, particularly the estimated infection rate, may, for example, determine the appropriate row (position on the y-axis) for defining a TRT solution space in FIGS. 3A-3E. In some embodiments, one or more individual-specific factors or community-specific factors may be used to help estimate the infection rate within a population to be tested. For example, the relative probability of infection may be calculated with respect to a larger population than the population to be tested (e.g., based on data for multiple previously tested populations) and the relative probability of infection for a specific population to be tested may be used to estimate a distribution of infected individuals and/or an infection rate within that population. Such information may be combined with prevalence testing results as described elsewhere herein.

In some embodiments, values for community-specific factors may be provided for a population to be tested. Community-specific factors may characterize the relative risk of infection for a community as a whole. Community-specific factors may relate to the social, spatial, demographic, economic, and/or political structure of a population to be tested, which may be correlated to a rate of infection spread. For instance, the rate of spread and number of infected individuals may vary between different geographic regions of a country. By way of example of a community-specific factor, where a population to be tested is a place of employment, community specific factors may include factors which characterize the relative risk of exposure within a natural setting, occupational setting, or other community setting (e.g., number of people at a facility, number of exposures to general public, physical distance between work stations, existence of protective safety measures, rehabilitation policies for infected individuals, etc.). In some instances, the value for a community-specific factor may be compiled from a plurality of values for individual-specific factors, such as a cumulative value or average value. In some instances, the value for a community-specific value may not be determinable from individual-specific values. In some embodiments, one or more community-specific values may be used to help determine an infection rate for a population to be tested, as described elsewhere herein. In some embodiments, one or more community-specific values may be used in adjusting the weights for individual-specific factors in calculating an SLI. For example, where weights are adjusted based on data collected from different populations, one or more community-specific factors may be used to adjust the weights differently for different populations.

The solution space of TRTs may be a function of one or more community insights. In some embodiments, the solution space of TRTs may be characterized as a function of both community insights (CI) and device insights (DI) (i.e., TRT=fn (CI, DI), where the community insight (e.g., estimated infection rate) and device insight (e.g., LOD) are independent variables which effectively define the solution space.

Values for individual-specific factors and/or community-specific factors may be collected or provided in various ways. In some embodiments, the values are provided as responses to questions (e.g., on a questionnaire). Individuals may be responsible for providing their own factor values or factor values may be ascertained by another individual. For example, values may be ascertained by one or more administrators for a population to be tested and/or by a third party. In some instances, values may be self-reported (either directly or indirectly). In some instances, values may be objectively ascertained or measured (e.g., a temperature may be taken by an administrator of the population). In some embodiments, a system may comprise a database of individuals. Individual-specific factor values may be stored for one or more individuals (e.g., in a database). At least some values for specific individuals may be updated periodically, optionally every time testing is performed. Some values may be used recurrently for multiple rounds of testing. In some embodiments, a value is stored and reused until updated by an individual, which may be voluntary. In some embodiments, factor values are input into the memory of a system via a remote electronic device (e.g., a computer, notebook, laptop, mobile device, etc.). The values may be input directly by an individual to be tested or indirectly by an administrator for a population. In some embodiments, the administrator may input unique sample identifiers for each individual a sample was collected from, particularly where the sample collection is done on-site (e.g., at a school or place of employment). In some embodiments, an individual may input a unique sample identifier (e.g., if sample collection is performed at home) upon sample collection. The unique sample identifier may be ascertainable (e.g., a visible serial number) on a sample collection container provided to the individual.

In some embodiments, samples from each population to be tested are confined to testing schemes that pools samples from within that population only. In some embodiments, samples from separate populations (e.g., separate parties or clients) may be intermixed to improve the efficiency of testing. For example, two or more populations may be combined during one or more rounds of testing. In other embodiments, samples may be intermixed between populations (e.g., according to SLIs), such that one or more samples from a first population may be pooled with samples from a second population and/or vice-versa. In various embodiments, one or more samples may be tested more than once (e.g., as a form of quality control).

Estimated Infection Rate within a Population to be Tested

In various embodiments of the systems and methods described herein, the selection of a particular testing scheme (e.g., which minimizes or is likely to minimize the TRT for testing a population), depends on the number of positive individuals within the population to be tested or the infection rate within that population. A more accurate estimate of the infection rate within the population to be tested can improve the ability to minimize the TRT. In some embodiments, the estimated infection rate for a population to be tested may be provided by an independent source (e.g., literature or public health agency data). For example, the prevalence rate may be estimated from testing waste water for levels of the pathogen, pathogen-derived material, or pathogen-related biomarkers. As another example, the estimated infection rate may be determined from mass testing of a population, which may or may not include at least some members of the population to be tested. See, e.g., Barber, Wired. 2020 Mar. 25 (available at https://www.wired.com/story/researchers-push-for-mass-blood-tests-as-a-covid-19-strategy/), which is herein incorporated by reference in its entirety. In some embodiments, the estimated infection rate for a population to be tested is measured specifically from samples collected within the population to be tested, referred to herein as prevalence testing. The estimated infection rate may be based on single sample testing of a plurality of individuals within the population. The estimated infection rate may be estimated based on pooled sample testing of a plurality of individual within the population to be tested. In embodiments in which prevalence testing is performed by pooled samples, the infection rate may be estimated from the test results for one or more pools. Additional testing for one or more mini-pools or individuals within the positive pools may or may not be performed. In other words, the prevalence testing may or may not be member-specific in that individuals sampled for measuring the infection rate may or may not be determined to be positive or negative for the infection of interest from the prevalence testing.

The pooling of samples for prevalence testing may be performed according to any of the methods described elsewhere herein (e.g., with respect to member-specific mass testing performed for community surveillance). In some embodiments, one or more administrators of a population to be tested (e.g., a school nurse for the testing of a school) may be trained to collect the samples, for prevalence testing or mass testing of a population, and/or to pool the samples, particularly for prevalence testing. In some embodiments, the signal obtained from prevalence testing one or more pooled samples may be used to estimate a distribution of positive individuals within the pool and/or the population to be tested such that an estimated infection rate can be calculated. The prevalence testing may preferably include asymptomatic (e.g., non-infected) individuals as well as infected individuals. The individuals selected for prevalence testing may be random. In some embodiments, the individuals selected for prevalence testing may be selected to replicate a distribution of individual-specific characteristics (e.g., as based on values for individual-specific factors for calculating an SLI). For example, in prevalence testing a school the proportion of teachers and students selected for prevalence testing may be chosen to resemble the proportion within the population to be tested at large or otherwise dependent on that proportion. Members with certain traits (e.g., teachers) may be preferentially grouped in the same pooled samples, may be relatively evenly distributed across pooled samples, or may be randomly distributed across pooled samples. In some embodiments, the estimated infection rate may take into account certain the presence of members in the population to be tested belonging to specific occupational groups that are at high risk of exposure to infection, such as doctors, nurses, institutional staff at healthcare facilities, nursing home residents and staff, grocery store/chain employees, sanitation workers, teachers and staff of schools & colleges, and other groups that form the essential workforce of an economy. The test results from prevalence testing may be used to generate, calculate, or fine-tune an SLI in later rounds of testing (e.g., member-specific mass testing). For instance, different infection rates between students and teachers determined from prevalence of infection may be used to adjust the weight of individual-specific factor values in later rounds of testing (e.g., a factor value that distinguishes between teachers and students or a factor value related to age). The prevalence testing may be considered a "pilot" round of testing for subsequent rounds of member-specific mass testing.

The selection of individuals within any specific category (e.g., teachers or students) may be random. In some embodiments, a system, as described elsewhere herein, may be programmed to randomly select individuals for prevalence testing and may use stored factor values to select individuals according to any predetermined distributions. The system may be configured to communicate (e.g., send a message to a remote device) the selection to one or more administrators of a population to be tested.

In some embodiments, at least about 0.01%, 0.05%, 0.1%, 0.5%, 1%, 2%, 3%, 4%, 5%, or 10% of the population to be mass tested is first sampled for estimation of the infection rate within the population. In some embodiments, individual samples for mass testing the population to be tested via member-specific community surveillance are collected no later than 1 day, 2 days, 3 days, 4 days, 5 days, or 6 days after the samples for estimated the infection rate are collected. In some embodiments, the prevalence testing is performed on the same day as the mass testing. The samples used for the prevalence testing may be the same samples or different samples. If single sample testing is performed for the prevalence testing, the tested members may be removed from the subsequent round of mass testing as the single sample testing can provide member-specific results.

In some embodiments, the same assay is used to perform the prevalence testing as the mass testing performed for community surveillance. In some embodiments, the assay used to perform the prevalence testing is more sensitive (i.e., has a lower LOD) than the assay used to perform the mass testing. In some embodiments, if different assays are used to perform the mass testing, the assay used to perform the prevalence testing may have a lower LOD than at least one of the assays or a lower LOD than all the assays. In some embodiments, the assay used to perform the prevalence testing may have an LOD no greater than about 40, 50, 60, 70, 80, 90, 100, 110, 120, 130, 140, 150, 160, 170, 180, 190, or 200 copies/mL. For example, in some embodiments, the assay used to perform the prevalence testing may have an LOD no greater than about 100 copies/mL. In some embodiments, the assay used to perform the prevalence testing may have an LOD no greater than about 1, 2, 3, 4, 5, 6, 7, 8, 9, 10, 15, 20, or 25 copies/reaction. For example, in some embodiments, the assay used to perform the prevalence testing may have an LOD no greater than about 3 copies/reaction. In some embodiments, single sample testing of every individual is recommended (as opposed to pooled sample testing) if the infection rate within a community is greater than about 1%, 5%, 10%, 15%, 20%, 25%, or 30%. For example, single sample testing of every individual may be recommended if the infection rate within a community is greater than about 25%.

In some embodiments, prevalence testing within a population to be tested is performed prior to each of multiple rounds of mass testing (e.g., pooled sample testing). For example, prevalence testing may be performed prior to each round of mass testing. In some embodiments, prevalence testing is performed at regular intervals (e.g., once every month or prior to every other round of mass testing). In some embodiments, the estimated infection rate used for designing or selecting a testing scheme for a particular round of mass testing is provided from a prior round of prevalence testing. For example, the estimated infection rate determined from a round of prevalence testing may be stored on memory (e.g., on a database comprising populations) and used by the methods or systems disclosed herein until updated. In some embodiments, the infection rate may be updated based on one or more prior rounds of mass testing within a population that has already been tested. For instance, an estimated infection rate may be determined from the number of individuals assigned a positive infection status within a tested population and that estimated infection rate may be used during the next round of mass testing or all future rounds until updated.

Simulations

The selection of an efficient testing strategy, particularly an efficient pooled sample testing strategy, may be improved or optimized by the use of one or more computer-based simulations (i.e., a simulator). Simulations may replicate realistic results given unknown variables for specific populations to be tested (e.g., infection rates, infection level (e.g., viral density) distributions within infected individuals, distributions of positive individuals within pooled samples, etc.). Simulations can model complex population distributions and capture correlations between individual and/or population characteristics and infection probabilities (e.g., via machine learning methodologies) that cannot be mathematically derived. Simulations may better replicate the likelihood of actual test results at larger population sizes. For example, the simulated population may comprise at least 100, 500, 1,000, 5,000, or 10,000 members. Simulated distributions of infected individuals within a population of a given size (e.g., simulating individuals as positive/negative for an infection of interest and/or simulating individuals as having a certain amount or level of infection) may allow better predictions of testing outcomes, such as, but not limited to, TRT, false negatives, false positives, and/or cost savings. The predictions may comprise a most likely outcome and/or a probability or relative probability of one or more specific testing outcomes. The frequency distributions of infection levels may focus on stratifying a lower end of the infection spectrum. In some embodiments, the lower 5%, 10%, 15%, 20%, 25%, 30%, 35%, or 40% of a distribution of an infection level (e.g., viral load) may be stratified into 1, 2, 3, 4, 5, 6, 7, 8, 9, 10, or more classes. The probability of each bin/class/stratification may be determined or estimated as described elsewhere herein, including the examples. For example, in some embodiments, a lower portion of a frequency distribution for an infection comprising between about 10% and 35% of the range of the distribution may comprise at least 1, 2, 3, 4, 5, 6, 7, 8, 9, or 10 classes.

In some embodiments, a simulated distribution of positive individuals (may be used to simulate the distribution (e.g., random distribution) of those individuals within a plurality of pools of one or more sizes. The number of infected individuals may be predetermined by an input infection rate or may be simulated based on an input infection rate (i.e., each simulated individual is independently determined whether to have the infection based on a probability). Where applicable, the level of infection in an infected individual may be predetermined by a probability (i.e., multiply the probability by the total population size) or may be simulated based on the input probability (i.e., the infection level of each simulated individual is independently determined). The simulated distribution within pools may be used to predict one or more testing outcomes. The number of pools tested in each simulation may be at least about 100, 200, 300, 400, 500, 600, 700, 800, 900, 1,000, 2,000, 3,000, 4,000, 5,000, or 10,000 pools. In some embodiments, the positive individuals may be assigned a particular level or category of infection (e.g., a binned range of infection values, such as copies/mL). The distribution of individuals within the pools may be used to determine different testing outcomes for different testing schemes where the assay's ability to identify the individual as positive or negative is dependent on the infection level (e.g., an assay's LOD is expected to only allow detection of individuals having an infection level above a certain threshold). In some embodiments, the infection rate may be an independent variable input into the simulation. In some embodiments, the infection rate (and number of infected individuals within the simulated population) may be determined by the simulator. The simulation may comprise one or more input variables, including but not limited to: infection rate, total population size, pool size, number of pools, LOD (for one or more pool sizes), capture rate or probability of false negatives, the probability of infection, the probability of a given level of infection, etc.

In some embodiments, the distribution can be used to estimate an infection rate for a population based on test results for one or more pooled samples from the population. For instance, the testing results for one or more pools of samples may be compared to simulated tests results for various infection rates and the most likely infection rate or range of infection rates within the population determined.

In various embodiments, the simulations may be based on one or more real-life data sets. The data sets may comprise actual test results (e.g., positive/negative and/or specific values) for real individuals. The data sets may comprise additional information associated with one or more of the test results, such as patient-specific information, population-specific information, and/or assay information. The data sets may comprise information or values related to any individual-specific or community-specific factors described elsewhere herein. Correlations between the test results and any additional information may be used to alter probabilities of infection in simulated individuals. For example, in various embodiments, a correlation may be found in analyzed data between family size and likelihood of infection. When simulating individuals of a different population, the family size of each simulated individual may be used to assign a probability of infection, which the simulator may use in simulating an infection status for the simulated individual. In some embodiments, the simulation may replicate the sorting of individuals into positions on a hierarchy based on factor values, as described elsewhere herein, and the predicted improvement in testing results may be ascertained.

Data sets for modeling distributions may comprise infected patients and/or non-infected patients. Data sets may comprise symptomatic patients and/or asymptomatic patients. Data sets may comprise susceptible patients and/or non-susceptible patients (e.g., immunized patients). The probabilities used in a simulation may be adjusted to account for any biases in the data sets (e.g., the distributions of infection levels may be adjusted downwards in a distribution modeled from symptomatic test results to account for asymptomatic patients in the population).

The simulations may be performed in a manner such as that described in detail in the examples herein or any other suitable manner. The simulations may simulate distributions within hierarchies comprising only a base pool and no mini-pools or may simulate one or more hierarchies having multiple levels of pools. The simulations may use a loop algorithm based on the simulation of a single pool hierarchy to simulate the testing of a multi-pool hierarchy. Methodologies for modifying the simulator described in the examples herein to replicate a multi-pool hierarchy structure are well known in the art.

Systems for Community Surveillance

Disclosed herein are systems for performing one or more of the methods described herein. The systems may automate one or more of the steps of the methods described herein. The system may comprise one or more processors operatively coupled to one or more memories. The one or more memories may store data and/or code for executing one or more steps or functions related to the methods described herein. One or more electronic devices may comprise a memory and/or a processor of the system. Examples of electronic devices include, but are not limited to mobile devices, PCs, laptops, and other computational devices. Such electronic devices can store and communicate (internally and/or with other electronic devices over a network) code and data using computer-readable media, such as non-transitory computer-readable storage media (e.g., magnetic disks; optical disks; random access memory; read only memory; flash memory devices; phase-change memory) and transitory computer-readable transmission media (e.g., electrical, optical, acoustical or other form of propagated signals—such as carrier waves, infrared signals, digital signals). One or more of the system components may be part of one or more servers. One or more servers may be cloud-based servers. A server may be connected to one or more electronic devices over a network and may comprise hardware and/or software for executing one or more of the functions performed by the one or more processors of the system. The functions may be performed by processing logic that comprises hardware (e.g., circuitry, dedicated logic, etc.), firmware, software (e.g., embodied on a non-transitory computer readable medium), or a combination thereof. Operations described may be performed in any sequential order or in parallel, unless dictated otherwise by context.

The system may comprise a central processing device or server for performing one or more of the steps of the methods described herein, including, for example, one or more of sample tracking, tracking of individual test results, tracking of population compositions (i.e., which individuals are associated with which populations), generating TRT solution spaces and/or numbers or probabilities associated therewith (e.g., minimum TRT and/or probability of achieving minimum TRT), designing pooled sample testing schemes (e.g., hierarchy structures), performing simulations of positive individual distributions, determining optimal testing schemes (e.g., base pool sizes for pooled sampling), populating pooled sample hierarchies (i.e., assigning individuals to specific positions within one or more hierarchies), calculating weight values for SLIs (e.g., using a feedback algorithm), calculating SLIs, compiling and/or reporting test results, and storing data or information related to any of these steps. In various embodiments, in which a user or system selects an optimal testing scheme, additional factors other than the TRT may be considered. For example, the performance characteristics of the particular assay (e.g., an RT-PCR assay), the speed with which the test results of infection status are delivered to the tested population, the price per test and quantity discounts, if any, may be considered. In some implementations, the system may be programmed to automatically account for such factors. For instance, the insights gained on such parameters and the price-breaks offered by manufacturers of the test kits and the companies offering analytical services may be used in determining sample sizes for compositing.

The system may comprise one or more databases for facilitating the implementation of the methods described herein. The one or more databases may be stored on the same memory or on different memory. The memories may be operatively coupled to the central processing device. The processing device and databases may be part of a central computing device or server. The system may comprise one or more of the following databases: a database of individuals, a database of populations (e.g., clients), a database of samples, a database of hierarchies, a database of test results, a database of testing facilities and/or testing machines, a database of assays, a database of simulation results, etc. The information or data stored in each database may not be mutually exclusive to other databases. The databases may comprise pointers to other databases or items within other databases, creating a linked network of information. Any database may comprise a linker to one or more items in any other database.

The database of individuals may comprise entries for each individual that is involved in a community surveillance (e.g., mass testing) testing scheme. There may be multiple databases of individuals (e.g., one for each population to be tested) or a cumulative database of individuals which may comprise individuals from distinct populations for testing. The information associated with each individual may comprise one or more of: a unique individual identifier (i.e., a unique patient identifier), a name, a date of birth (or other bibliographic information), demographic information, one or more unique population identifiers (for each population the individual is associated with), one or more individual-specific factor values, individual infection status (e.g., positive or negative), and linkers to any other database (e.g., a test results database, sample database, or population database). A unique individual identifier (e.g., a patient identification number) may be assigned to each individual for tracking. The unique individual identifier may effectively allow tracking of individuals without use of personal-identification information.

The database of populations may comprise entries for each population for which surveillance testing is performed. The information associated with each population may comprise one or more of: a unique population identifier (e.g., a population/client account number), the individual members of the population (e.g., a list of unique individual identifiers and/or pointers to entries in the database of individuals), a population size, a population testing strategy (e.g., frequency of testing), identities of one or more population administrators, and a pending testing status (e.g., awaiting sample collection, samples collected, samples, received, samples tested, awaiting test results, etc.).

The database of samples may comprise entries for each individual sample collected from an individual. The database may comprise entries for pooled samples (e.g., samples pooled at the site of collection or samples pooled during the processing/testing of samples). The samples may be assigned a unique sample identifier such that samples can be tracked. The unique sample identifier may allow tracking of the sample without using personal identifying information of the individual from which the sample was collected. The sample identifier may be physically associated with a collection tube or container and/or any other subsequent container the sample may be transferred into for processing. For example, the unique sample identifier may be determinable by a barcode or RFID device (e.g., a transponder). In some embodiments, the sample is assigned a new or additional unique sample identifier when transferred to a new container. In some embodiments, a single unique sample identifier is used across all stages of the testing. The unique sample identifiers may allow tracking of multiple samples across various stages and physical locations (e.g., facilities). The sample database may comprise information related to the type of sample (e.g., nasopharyngeal secretion, oropharyngeal secretion, blood, etc.) and/or a specific assay or type of assay that the sample (e.g., the sample container) is configured for. The sample database may comprise a sample status (e.g., awaiting collection, in transit, awaiting processing, processed/awaiting testing, testing complete, disposed, etc.).

In some embodiments, a database of hierarchies may be used to track the positioning of specific samples and/or individuals within a hierarchy structure designed for testing, including the precise positioning of each sample/individual within the hierarchy. Hierarchy entries may be generated, for example, for every round of surveillance testing according to the hierarchy sizes and structures determined by the system.

A database of test results may comprise a status for each test run (e.g., pending, positive, negative, inconclusive, etc.).

The database may also comprise raw results for each test run (e.g., counts/volume) for one or more replicates.

A database of testing facilities and/or testing machines may comprise unique tester identifiers, for example, where multiple contracting facilities are used to perform the testing of one or more populations. The database may comprise information about the specific testing equipment used (e.g., the type of RT-PCR machine) and/or the serial number/model number of the testing equipment (e.g., the testing machine). The database may comprise information regarding the testing capacity of each machine or facility (e.g., a schedule of tests and/or number of testing slots available).

A database of assays may comprise information on the type of assay used (e.g., manufacturing information and/or contact info, the sensitivity of the assay, the specificity of the assay, the LOD of the assay, etc.). The database may comprise inventory information for each type of assay (e.g., the number of assays available and/or their location).

The system may comprise one or more first remote electronic devices (referred to herein as "client devices") that are remote from the central processing device and memory. The client devices, for instance may be generic computers, notebooks, mobile phones, or any other type of electronic device that enables the client device to connect to the central processing device (e.g., on a server) via the internet (e.g., over a network). The client devices may be used by populations to be tested, such as by individuals within the population and/or population administrators. The client devices may allow the input of information for transmission to the central processing device and/or receipt of information transmitted from the central processing device. For instance, client devices may allow the input of information or data related to a factor value indicative of a relative probability of infection for an individual, a factor value indicative of a relative probability of infection for the population, a size of the population, a unique identifier for an individual within the population, a unique identifier for the population, one or more unique sample identifiers for collected samples, and/or an estimated infection rate. The client devices may be programmed to receive information or data related to an individual test result, test results for the population, and/or an estimated infection rate for the population. The client devices may share information or data with the central processing device over a web-based platform (e.g., hosted on a server). The client devices may use an application downloaded to the device to interact with the central processing device.

The system may comprise one or more second electronic devices (referred to herein as "test center devices") that are remote from the central processing device and memory. The test center devices may be used to share information with the central processing device, particularly where the testing is performed by one or more third parties with respect to the party managing or overseeing the surveillance testing (i.e., controlling the central processing device). The test center devices may be programmed to receive testing instructions from the central processing device. The testing instructions may comprise instructions, for example, for pooling individual samples. The processing device may be programmed to associate unique sample identifiers for the samples to be tested to unique individual identifiers identifying the individuals from which the samples were collected, such that the testing center device may receive instructions for pooling samples according to unique sample identifiers without use of personal identifying information and/or without needing any knowledge of the precise pooled sample testing schemes being employed. The test center device may be configured for transmitting test results to the central processing device. The test center devices may share information or data with the central processing device over a web-based platform (e.g., hosted on a server). The test center devices may use an application downloaded to the device to interact with the central processing device. The test center devices may use the same network and/or application as the client devices. The test center devices may use a different network and/or application from the client devices. The test center device may be a computer or other electronic device that is integral with and/or operably coupled with a sample preparation machine and/or a testing device (i.e., a detection device), as described elsewhere herein.

The system may comprise one or more sample preparation machines which prepare one or more samples for testing. The one or more sample preparation machines may be operably coupled to the central processing device. The one or more sample preparation machines may be remote from central processing device but operably connected to the central processing device over the internet (e.g., over a network). The one or more sample preparation machines may not be directly coupled to the central processing device, but may be indirectly connected through a test center remote electronic device and/or a testing device, as described elsewhere herein. The sample preparation device may be configured for robotic pipetting and/or liquid handling. For example, the testing device may comprise a robot-driven pipetting system which enables rapid pooled-sample preparation, appropriate sequencing of the samples, and delivery of the same to a testing device (e.g., a PCR machine or antibody detection instrument). Examples of robotic pipetting devices and liquid handlers are well known in the art. The sample preparation device may be configured to prepare pooled samples according to received testing instructions. The sample preparation device may be configured to receive instructions from a test center remote electronic device or directly from the central processing device in the same manner as a test center remote electronic device. In some embodiments, the sample preparation device may be configured to physically sort samples (e.g., containers comprising samples) according to received testing instructions. The sample preparation device may be configured to identify samples (e.g., read a unique sample identifier associated with a sample container). In some embodiments, the sample preparation device comprises a barcode reader and/or an RFID reader for identifying a unique sample identifier associated with a sample.

The system may comprise one or more testing devices. The testing devices may comprise detectors for detecting signals generated by an assay. For example, the testing device may be a RT-PCR machine (e.g., a high through-put PCR machine) as is well known in the art. The one or more testing devices may be operably coupled to the central processing device. The one or more testing devices may be remote from central processing device but operably connected to the central processing device over the internet (e.g., over a network). The one or more testing devices may not be directly coupled to the central processing device, but may be indirectly connected through a test center remote electronic device and/or a sample preparation device, as described elsewhere herein. The testing device may be configured to transmit test results and/or raw data (e.g., signal detection units, such as fluorescence units, or corresponding amounts of the pathogen, pathogen-derived material, or pathogen-related biomarker) to the central processing device, directly or indirectly through a test center electronic device and/or sample preparation device. The central processing device may be programmed to associate received test results to appropriate samples, individuals, and/or populations. The central processing device may be programmed to store test results for each sample and/or each individual on memory (e.g., in a database). The central processing device may be configured to calculate an infection rate within a tested population from the data or test results received. The testing device may be configured to receive testing instructions from a test center remote electronic device, from a sample preparation device, and/or directly from the central processing device in the same manner as a test center remote electronic device. For example, the test instructions may comprise an order of samples to test. The test instructions may comprise an algorithm or code the testing device is configured to execute which implements a testing scheme (e.g., programming the device to test certain samples in response to prior test results). The sample preparation device may be configured to identify samples (e.g., read a unique sample identifier associated with a sample container). In some embodiments, the sample preparation device comprises a barcode reader and/or an RFID reader for identifying a unique sample identifier associated with a sample.

In various embodiments, a test center electronic device, a sample preparation machine, and a testing device may be an integral device or may be operably connected to a single computational device. In some embodiments, any two of a test center electronic device, a sample preparation machine, and a testing device may be an integral device or may be operably connected to a single computational device.

The system may comprise one or more software programs for automating the functions described herein. Some of the software programs may be commercially available programs. For example, the system may use custom or commercially available laboratory information management software to perform some of the tracking operations described herein. One or more web-based portals may be used for the sharing of information between different parties (e.g., between clients, operational managers, and testing facilities), as described elsewhere herein. In some embodiments, the system may comprise a "simulator" as described elsewhere herein for performing simulations (e.g., simulating one or more average TRTs for a given population size, testing scheme, and/or infection rate). The simulator may comprise software for performing the simulation. The software may be stored on memory. The simulator may comprise additional hardware components for performing the simulation (e.g., a processor and/or memory). The simulator may be part of the same device (e.g., computer or server) comprising the central processing device or may be a separate component. For example, the simulator may be a separate computer or server which is operably connected to the central processing device over the internet (e.g., over a network). The simulator may be used to generate values (e.g., average TRTs). The central processing device may use one or more simulated values (e.g., TRTs) to automate one or more of the functions (e.g., deciding on an optimal testing scheme) as described elsewhere herein. The simulator may be configured to transmit the one or more values to the central processing device. The values may be stored on a database as described elsewhere herein (e.g., as part of a taxonomy table). In some embodiments, the central processing device is configured to transmit data (e.g., input parameters) to the simulator. The simulator may be programmed to automatically return simulation results for the received data.

In various embodiments, test results may be forwarded to an automated report writer for generation of a comprehensive report describing the results of one or more rounds of surveillance testing for a population. The system may use a custom or commercially available automated report writing software executed by the central processing device or by the test center electronic device, sample preparation device, or testing device. The test results may also be used inform the community and/or the various assay or testing device manufacturers of the gains obtained by employing a surveillance testing strategy. The system may be configured to distribute periodic advisories that can inform users of this system (e.g., client populations, testing facilities, and/or manufacturers) of the benefits of their subscription.

In various embodiments, one or more of the steps may be performed manually. For instance, the sample may be manually pooled according to received testing instructions.

It will be understood that when a first system component is described as configured or programmed to send or transmit data or information to a second system component, the second system component can be understood to be configured or programmed to receive the data or information from the first system component. Likewise, when a first system component is described as configured or programmed to receive data or information from a second system component, the second system component can be understood to be configured or programmed to send or transmit the data or information to the first system component.

FIG. 4 schematically depicts an example of a system for automating one or more aspects of mass testing as described elsewhere herein. The testing system 2 may comprise various remote components which are operably connected to one another, such as over a network. Operable connections between components are depicted by double-sided arrows and allow the transmission and receipt of data between the components. The testing system 2 comprises a central processing device, server 4. The server 4 may comprise memory 6, a processor 8, and optionally a simulator 10. The memory 6 may store one or more databases 12, each of which may be one of the databases described elsewhere herein. The system 2 further comprises a test center device 14 (e.g., a computer), a sample preparation device 16 (e.g., a liquid handler), and a testing device 18 (e.g., an RT-PCR machine). The system may further comprise one or more client devices 20 that are remote from server 4. The client devices 20 may be operably connected to server 20 over a network.

In various embodiments, the test center device 14, sample preparation device 16, and testing device 18 are a single device. In various embodiments, test center device 14 and sample preparation device 16 are a single device. In various embodiments, test center device 14, and testing device 18 are a single device. In various embodiments, sample preparation device 16, and testing device 18 are a single device. In embodiments in which any of test center device 14, sample preparation device 16, and testing device 18 is not part of an integral device with the other two devices, it may be operably connected to at least one of the other two devices (e.g., over a wired connection or local network). In one embodiment, test center device 14, sample preparation device 16, and testing device 18 may be housed in a test center 22 which is remote from server 4 (e.g., where the test center and operational manager of the testing process are separate entities). Devices 14, 16, 18 of test center 22 may be operably connected over a network to server 4 through any one, two or three of the devices. In some embodiments, at least one of devices 14, 16, 18 is operably connected over a network to server 4. One or two of devices 14, 16, 18 may be indirectly connected to server 4 via a local connection to another one of devices 14, 16, 18, which is operably connected over a network. In one embodiment, the server 4 and devices 14, 16, 18 are housed in the same facility 24 such that server 4 is not remote to the testing center 20.

As depicted in FIG. 4, samples may be collected from individuals or populations associated with client devices 20 for testing at test center 22. For example, the samples may be delivered (e.g., mailed) from on-site collection locations to test center 22. In some embodiments, sample may be delivered indirectly to test center 22 through an operational manager in control of server 4. The operational manager or the test center 22 may deliver sample collection tools or equipment to the individuals or populations (e.g., administrators).

Information regarding the populations, individuals, and/or samples associated with client devices 20 may be transmitted to server 4, as described elsewhere herein. Server 4 may store information (e.g., unique sample identifiers, unique patient identifiers, individual-specific factor values, etc.) as needed on one or more of databases 12. For each population to be tested, the server 4 may automatically determine the optimal testing scheme according to any of the methods described elsewhere herein for one or more rounds of testing. Server 4 may access data on the databases 12 and/or generate data using the simulator 10 to make testing determinations. In some embodiments, the simulator 10 is remote from the server, but operably connected over a network. In some embodiments, simulator 10 is not used concurrently with an automated determination of an optimal testing scheme, but the server 4 accesses prior simulation results from a simulator 10 which are stored on a database 12.

Server 4 may transmit testing instructions to test center 22, via one or more of devices 14, 16, 18. In some embodiments, sample preparation device 16 is programmed to prepare pooled samples according to test instructions received from server 4 (e.g., pools samples associated with specified unique sample identifiers). The test instructions may program the sample preparation device 16 to pool certain samples in a manner contingent on real-time test results from testing device 18. In some embodiments, the sample preparation device 16 is programmed to automatically pool samples in response to test results from testing device 18. In some embodiments, testing device 18 intermittently transmits test results to server 4 (e.g., after testing samples at one level of a hierarchy) and sample preparation device 16 receives iterations of test instructions from server 4 based on processed or unprocessed test results transmitted to server 4 by testing device 18. In some embodiments, testing device 18 is programmed to receive testing instructions from server 4 (e.g., which samples to perform detection on). Testing device 18 may be programmed to transmit raw test results to server 4. Server 4 may use the information stored in databases 12 to automatically determine from the raw test results which individuals are positive/negative. Server 4 may store the test results on one or more of databases 12. Server 4 may be programmed to automatically generate a comprehensive test results report. Server 4 may be programmed to transmit (e.g., automatically) test results and/or a comprehensive test results report to the appropriate client devices 12 associated with the test results.

Long-Term Testing Strategies

Disclosed herein are comprehensive community-centered screening and infection control strategies. The strategies may comprise one or more rounds of mass testing (e.g., periodic pooled sample testing). The one or more rounds of testing may be member-specific. In some embodiments, periodic testing of a population may be performed on a regular or relatively regular basis. For example, a population may be mass tested approximately once every 1, 2, 3, 4, 5, or more weeks or once every 1, 2, 3, 4, 5, 6, or more months. Each round of mass testing may comprise a pooled sample testing scheme as described elsewhere herein. The design of each round of pooled sample testing (e.g., one or more of the base pool size(s), the hierarchy structure, the assay(s) used, etc.) may be independently determined during each round of mass testing, particularly if the estimated infection rate and/or community insight factors have been updated. In some embodiments, one or more rounds (e.g., subsequent rounds) of mass testing may implement the testing scheme. In some embodiments, some rounds of mass testing may comprise single sample testing if determined to be the most effective testing scheme (e.g., if the estimated infection rate is high, such as over 30%).

In some embodiments, single sample testing of every individual in the population may be performed periodically regardless of whether it is determined to be the most efficient testing scheme. For example, single sample testing may be performed at least once every 4, 5, 6, 7, 8, 9, or 10 weeks or at least every 1, 2, 3, 4, 5, or 6 months, in addition to other regular rounds of periodic mass testing. The single sample testing may or may not replace a round of mass testing via pooled sampling that is otherwise scheduled to take place at substantially the same time. Periodic single sample testing may be performed at a frequency less than that of mass testing performed according to the most efficient testing scheme (e.g., pooled sample testing). Periodic single sample testing may provide a measure of quality control over pooled sample testing. Rounds of single sample testing may be used to provide an estimated infection rate within a population for subsequent rounds of mass testing. Furthermore, the additional assurance provided by periodic single sample testing may allow regular intervals of pooled sample testing to be spaced further apart, which may ultimately reduce the TRT required for a population over a period of time.

In particular embodiments, a testing scheme may comprise single sample testing approximately once a month in addition to the most efficient form of mass testing (e.g., pooled sample testing) approximately once a week. In various embodiments, a testing strategy may be implemented until the infection rate in a community is brought below a certain threshold. The testing strategy (e.g., the frequency of various types of testing) may be adjusted over time (e.g., based on the infection rate within the population). The members of a population may or may not be completely identical between each round of testing. For example, former employees may be removed from an employment-based population to be tested and new employees may be added. Furthermore, some members of a population who are determined not to be susceptible to infection may be selectively excluded from one or more rounds of testing (e.g., vaccinated individuals or individuals who have been identified as positive within a prior predetermined time frame, such as 1-6 months).

In some implementations, the cost of performing mass testing within a population may be reduced by approximately 93-95%. In some implementations, the spread of an infection of interest within a population may be effectively contained (e.g., the infection rate may be stabilized or begin to decrease) within approximately 7-10 days after implementing a mass testing strategy as described herein. For instance, by repeating the mass testing process every week, a population may be able to bring the infection rate of SARS-CoV-2 under 0.01% within the following 2-3 weeks.

In various embodiments, an individual may be treated for an infection of interest based on the assignment of a positive infection status from one or more tests described herein.

Treatment may comprise quarantining or isolating the positive individual (at least from the population to be tested) until the risk of transmission has substantially expired. For instance, an individual assigned a positive status for SARS-CoV-2 may be quarantined for at least about 10-14 days and/or until a test result assigning a negative infection status is received. Other routine treatments for individuals infected with infections, such as SARS-CoV-2 are well known in the art. Individuals who are assigned a negative infection status may be allowed to presume normal activities and interpersonal interactions within their respective community. For instance, where a population to be tested is a place of employment, negative individuals may be allowed to work "on-site." In some embodiments, temporary rounds of quarantine or isolation (e.g., "work from home") may be instituted for all individuals to be tested or recently tested individuals until test results are received. Contact tracing may be performed within the population based on the identification of positive individuals. Contact tracing may rely on information stored in one or more databases described elsewhere herein. For instance, contact tracing may alert individuals of a potential exposure to the contagion. Contact tracing may be performed without identifying positive individual of their positive test result. Rehabilitation strategies may be performed following evidence generated by mass testing. Individuals with positive test results may be interviewed for additional information.

EXAMPLES

Example 1: Questionnaire of Individual-Specific Community Insight Factors for Calculating SLI Each individual member of a population to be tested is provided the questionnaire illustrated in Table 4 below. The individual fills out the questionnaire and provides the completed questionnaire to an administrator of the population, either before or shortly after a sample is collected from the individual for mass testing (e.g., via e-mail and/or physical collection). The administrator collects the questionnaires, optionally checking them for completion, and returns them to the testing facility or third party operational manager of the community surveillance process (e.g., via e-mail or mail). Alternatively, each individual member of the population to be tested is granted access to a user web-based portal which allows them to create a personal account or profile associated with an account of the population to be tested and the individual is able to directly enter the responses via a user interface (e.g., via the keyboard or touch-screen display of an electronic device). The administrator may also enter the individual responses into the web-based portal via an administrator account.

TABLE 4

Individual questionnaire for calculating relative probability of infection (SLI)

Personal health assessment

Your name: _____
    1. Age: ____
    2. Gender: ____
    3. Family: Number of people living at your residence
    4. Pre-existing conditions: Yes or No, check all those apply,
        a. Cancer ____
        b. Chronic kidney disease ____
        c. COPD (chronic obstructive pulmonary disease) ____
        d. Immunocompromised state from organ transplant ____
        e. Obesity (body mass index of 30 or higher) ____
        f. Serious heart conditions ____
        g. Sickle cell disease ____
        h. Type 2 diabetes mellitus ____

Work environment

5. Since your last day of work, or last visit here, have you had any of these symptoms that is not attributable to another condition?
    6. Have you had a positive-COVID test for active virus in the past 10 days? yes or no
    7. Do you have of these symptoms that you cannot attribute to another condition?
        a. Fever or chills, yes or no
        b. Cough, yes or no
        c. Shortness of breath or difficulty breathing, yes or no
        d. Fatigue, yes or no
        e. Muscle or body aches, yes or no
        f. Headache Yes or no
        g. Recent onset of loss of taste or smell, yes or no
        h. Sore throat, yes or no
        i. Congestion, yes or no
        j. Nausea or vomiting, yes or no
        k. Diarrhea, yes or no Socio-economic and demographic insights 8a. Do you wear a face cover when you go out? yes or no
        b. If yes, what percent of the time? ____
    9a. Do you adhere to maintaining a social distance of 6 feet when you go out? yes or no
        b. If yes, what percent of the time? ____
*For the following questions, contact is defined as being within 6 feet (2 meters) for more than 15 minutes with a person, or having direct contact with infectious fluids from a person (for example being coughed or sneezed on). Within a time-frame of the last 10 days,
    10. Have you had contact with anyone who was diagnosed with COVID-19? yes or no
    11. Have you had contact with a staff of a long-term nursing care facility? yes or no
    12. Have you had contact with a resident of a long-term nursing care facility? yes or no TABLE 4-continued Individual questionnaire for calculating relative probability of infection (SLI)

13. Have you had contact with an employee of a meat-processing plant? yes or no
14. Have you had contact with anyone who had been incarcerated in a prison? yes or no
15. Have you been to a restaurant(s), If yes, how often? ____
    a. What are their estimated seating capacities? [small, medium, large]
16. Have you been to a grocery store, If yes, how often? ____
    a. What are their estimated sizes of the stores? [small, medium, large]
17. Have you been to a shopping mall, If yes, how often? ____
    a. What are their estimated sizes of the malls? [small, medium, large]
18. Have you been to a movie theater, If yes, how often? ____
    a. What are their estimated seating capacities? [small, medium, large]
19. Have your partied on a beach with friends and family? If yes, how often? ____
20. Have you attended a performance (an opera, a choir, etc.), If yes, how often? ____
    a. What are their estimated seating capacities? [small, medium, large]
21. Have you attended a church wedding, If yes, how often? ____
    a. What are their estimated seating capacities? [small, medium, large]
22. Have you hosted any birthday parties in your residence, If yes, how often? ____
    a. What are their estimated capacities? [small, medium, large]
23. Have you hosted any functions your residence (other than birthday parties), If yes, how often? ____
    a. What are their estimated capacities? [small, medium, large]
24. Have you attended any birthday parties, If yes, how often? ____
    a. What are their estimated capacities? [small, medium, large]
25. Have you attended any events (other than birthday parties), If yes, how often? ____
    a. What are their estimated capacities? [small, medium, large]
26. Have you attended any funeral services, If yes, how often? ____
    a. What are their estimated capacities? [small, medium, large]
27. Have you hosted any family gatherings other than the above, If yes, how often? ____
    a. What are their estimated capacities? [small, medium, large]
28. Have you attended any family gatherings, If yes, how often? ____
    a. What are their estimated capacities? [small, medium, large]
29. Have you started going back to work? If yes, what is your mode of transport? ____
    ____walk ____car ____bike ____motorbike ____bus ____train ____tram ____ferry
    a. How long does it take to get to work? ____

Upon receiving all the completed questionnaire responses or by a given deadline by which time testing procedures must be initiated, a processor automatically calculates an SLI value for each member who completed the questionnaire. The SLI for each member may be calculated according to Formula III, disclosed elsewhere herein. For factors that posed yes or no questions, 0 may be assigned as a factor value for no answers and 1 may be assigned a factor value for yes answers. For factors that posed small, medium, or large questions, 1, 2, and 3 may be assigned as factor values for small, medium, and large, respectively. For factors that asked for a selection of options, an algorithm may assign an ordinal value (e.g., 1-6 for 6 available options) based on which option poses the greatest risk of exposure to infection. The processor ranks all the members in the population to be tested in order of decreasing SLI and assigns each individual in the population to be tested a ranking in a database of individuals within the population.

Example 2: Simulating Distribution of SARS-CoV-2 Viral Loads in Symptomatic Populations Two de-identified Covid-19 datasets measuring the viral density of SARS-CoV-2 in symptomatic populations of individuals collected during the Covid-19 pandemic during the weeks of March to April of 2020 were obtained. The datasets can be found in Kleiboecker et al. J Clin Virol. 2020 August; 129:104439 (doi: 10.1016/j.jcv.2020.104439) which is herein incorporated by reference in its entirety, and in which 4,428 infections were identified from 29,713 symptomatic samples tested with an RT-PCR assay having an LOD of 78 copies/mL; and Arnaout et al., bioRxiv. 2020 Jun. 4; 2020.06.02.131144 (doi: 10.1101/2020.06.02.131144), which is herein incorporated by reference in its entirety, and in which 4,774 infections were identified from 20,076 symptomatic samples tested with an RT-PCR assay having an LOD of 100 copies/mL. Together, the datasets represent a total of 9,202 individual measurements from infected individuals. Histograms of the frequency distributions across binned viral densities within the infected individuals are reproduced in FIGS. 5A and 5B, for the Kleiboecker study and the Arnaout study, respectively. Due to exponential viral growth within a matter of days (e.g., from 1 to 1011), viral concentration data are generally presented in log 10 scale for ease of visualization.

Figure 5A:
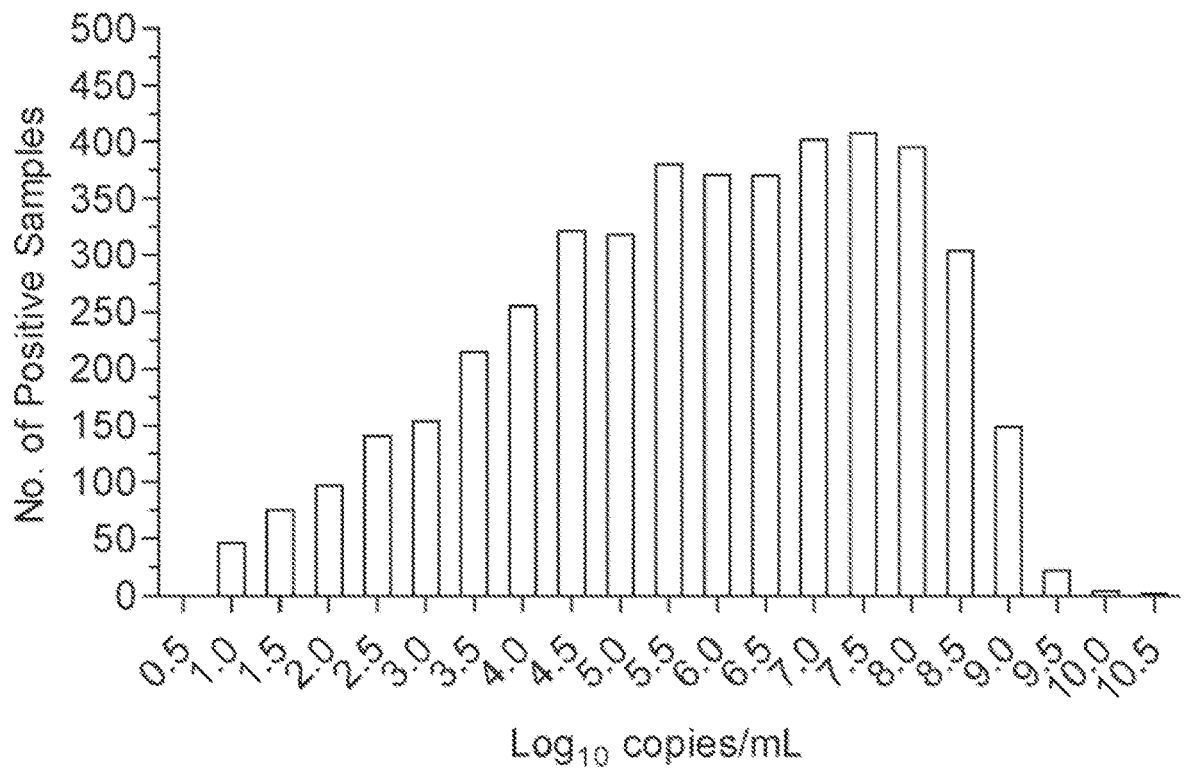
FIGS. 5A and 5B each depict histograms illustrating the distribution of viral density of SARS-CoV-2 in a population of symptomatic individuals.
Figure 5B:
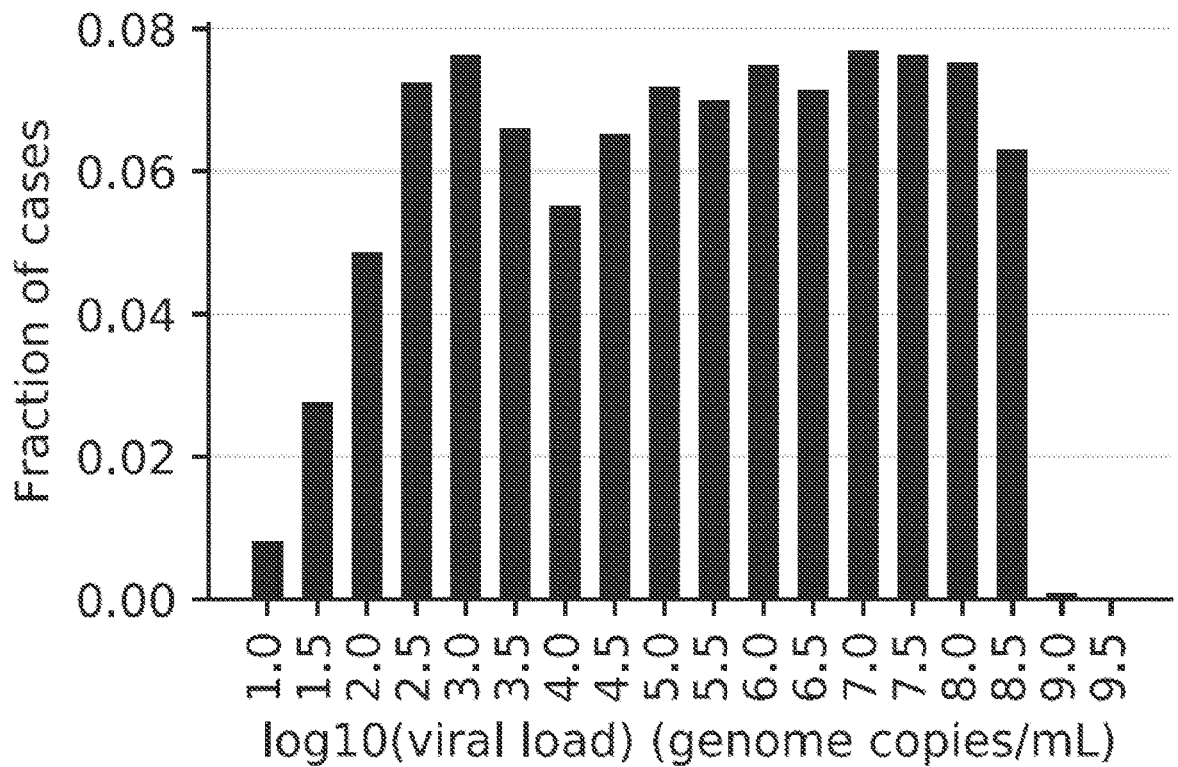

Based on the data presented in FIGS. 5A and 5B, a table of unweighted average frequencies (of estimated percent in class) was constructed for various viral density bins (quantified by genome copy equivalents (GCEs)) as found in Table 5 below. The viral density bins stratify viral loads at the lower end of the spectrum into 7 classes or bins where various assays may miss detection of an infection due to the low viral density (e.g., the density in a biological specimen may be below the LOD of an assay).

TABLE 5

Frequency classes for low viral density infections

| Freq Class | Range of Log10 GCE/mL | Range of GCE/mL | Est. Freq (Kleiboecher) | Est. % in class (Kleiboecher) | Est. % in class (Arnaout) | Avg |
| --- | --- | --- | --- | --- | --- | --- |
| 1 | 0.25-0.75 | 2-6 | 0 | 0.000 | 0.000 | 0.0000 |
| 2 | 0.75-1.25 | 6-18 | 50 | 0.011 | 0.006 | 0.0086 |
| 3 | 1.25-1.75 | 18-56 | 75 | 0.017 | 0.026 | 0.0215 |
| 4 | 1.75-2.25 | 56-178 | 92 | 0.021 | 0.048 | 0.0344 |
| 5 | 2.25-2.75 | 178-562 | 140 | 0.032 | 0.073 | 0.0523 |
| 6 | 2.75-3.25 | 562-1778 | 162 | 0.037 | 0.076 | 0.0563 |
| 7 | 3.25-3.75 | 1778-5623 | 215 | 0.049 | 0.064 | 0.0563 |
| Totals: | | | 734 | 0.17 | 0.29 | 0.23 |

Weighted estimates were not calculated due to several complicating factors such as the number of labs involved, weeks of data collection, and other issues specific to individual studies. The bottom row (totals) indicates the average percentage of SARS-CoV-2 infected individuals in the population who reside in the lower end of the viral measurement spectrum as defined by the upper cutoff of frequency class 7 (3.75 log 10 GCE/mL or 5,623 GCE/mL). Individuals assigned false negatives and/or asymptomatic infected individuals are more likely to have viral loads in the lower end of the spectrum (e.g., in one of classes 1-7) along with uninfected individuals (true negatives). As defined by Table 5, this lower proportion of the spectrum accounts for approximately 23% of infected individuals (or at least 23% of symptomatic infected individuals). An eighth class (class 8) was also effectively constructed for all individuals having viral densities greater than the upper cutoff of class 7. As seen in FIGS. 5A and 5B, this upper class may represent the majority of infected individuals (approximately 77% of infected individuals as defined by the cutoffs of Table 5). The use of the simulator is not limited to this dataset. Any suitable dataset(s) may be used to construct frequency classes. The precise number and cutoffs for the frequency classes may be varied as well without deviating from the scope of this disclosure.

A simulator was constructed to simulate the viral loads in a population of variable size according to the frequency distributions of Table 5. The simulator defined four multinomial classes of infection, referred to herein as Black, Brown, Blue, and Red. Class Black collapsed Frequency Classes 1-5 into a single class; Class Brown equated to Frequency Class 6, Class Blue equated to Frequency Class 7, and Class Red equated to Frequency Class 8. The simulator also defined a Class Green to capture uninfected individuals. The simulator accepted infection rate, total population size, pool size, and number of pools as independent variables. The particular infection class (Black, Brown, Blue, Red, Green) of each of the simulated individuals was independently assigned by the simulator via the infection rate and probabilities determined from Table 5. In other words, the simulator assigned each simulated individual to an infection class (Black, Brown, Blue, Red, Green) via a probabilistic determination (e.g., using a weighted random number generator, with user-provided weights). The simulator on average assigns an individual to Class Green (uninfected) a percentage of the time calculated from the infection rate (i.e., 1-IR). The simulator on average assigns an individual to one of Classes Black, Brown, Blue, or Red a percentage of the time calculated from a combination of the infection rate and the frequency distribution determined from Table 5 (Black—11.7%; Brown—5.6%; Blue—5.6%; and Red—77.1%). For example, on average the simulator assigns an individual to Class Red a percentage of the time corresponding to IR×0.771. Alternatively, the total number of infected and non-infected individuals could be strictly set by the infection rate and only the infected individuals (Classes Black, Brown, Blue, and Red) could be stochastically distributed amongst classes via an independent probabilistic determination based on the frequencies of Table 5. The simulator then randomly distributed the individuals into the number of pools of set pool size inputted into the simulator. For most simulations, the number of pools was set as the total population divided by the pool size and the total population size was selected to evenly distributed the simulated members of the population, each into one pool.

Based on the simulated distribution of individuals into various pools, the pool composition was determined for each pool (i.e., the number of individuals in each class—Black, Brown, Blue, Red, Green). Subsequently, the frequency for each possible distribution was calculated (for this particular simulation, the particular positioning of the individual within the pool was not considered). This simulator was used to estimate the TRT for identifying the positive individuals within the simulated population assuming that the simulated individuals of each pool would each be tested when and only if the pool first tested positive. For each simulated pool the TRT was calculated as 1 if no positive (Black, Brown, Blue, Red) individuals were assigned to the pool (i.e., one test performed on the pooled sample) or 1+pool size if any positive individuals were assigned to the pool (i.e., one test performed on the pooled sample and 1 test subsequently performed on each of the simulated individuals). This strategy may represent the base case analysis in situations where the time from test-to-decision is minimized (i.e., testing is not performed on mini-pools which may further reduce the TRT but which generally requires additional processing time). As described elsewhere, in a highly coordinated networked system, a sequential strategy can be employed and the number of tests could be significantly less than (1+pool size). The calculated TRT for each potential pool distribution was multiplied by the frequency of the pool distribution to determine a cumulative TRT for each type of pool distribution (which depends on the number of pools). The cumulative TRT for each type of pool distribution was then added to determine a total TRT for the simulated population. The simulation was performed a total of three times and the total TRT for the population was calculated as an average of the three replications. The number of replications and the size of the simulations can be altered to reach a level of confidence specified by the user. The random numbers were selected from a simulator that provides a number between 1 and a million, the numbers being designated to Class bins based on the appropriate probability.

The simulation was conducted for populations of 10,000 and 32,000 simulated individuals with pool sizes of 16 or 32 individuals for infection rates between 0.01% to 25% at various intervals and taxonomy tables were constructed depicting the estimated TRT for the population as a whole at each infection rate and pool size combination. Results for smaller size populations (e.g., 10,000 individuals) were pro-rated from results for larger populations (e.g., 32,000 individuals). Table 6 below illustrates representative results for three replicates of a 10,000-member population simulation and three replicates of a 32,000-member population at 16-sample and 32-sample pool sizes each. Because the total simulated population was large with respect to pool size, replicate sampling was performed without replacement (i.e., without re-simulating the infection status of the individuals). In other embodiments, replicate sampling may be performed with replacement.

TABLE 6

Simulated TRTs for 10,000-member and 32,000-member populations using 16-sample and 32-sample pools

| Infection Rate (IR) (%) | Total Tests Required (TRT) | | | |
|---|---|---|---|---|
| | Total Population Size = 10,000 | | Total Population Size = 32,000 | |
| | Pool Size = 16 | Pool Size = 32 | Pool Size = 16 | Pool Size = 32 |
| 0.01 | 630 | 336 | 2,016 | 1,075 |
| 0.02 | 635 | 346 | 2,032 | 1,107 |
| 0.03 | 675 | 379 | 2,160 | 1,213 |
| 0.04 | 680 | 399 | 2,176 | 1,277 |
| 0.05 | 693 | 419 | 2,216 | 1,341 |
| 0.06 | 705 | 473 | 2,256 | 1,512 |
| 0.07 | 730 | 503 | 2,336 | 1,608 |
| 0.08 | 755 | 533 | 2,416 | 1,704 |
| 0.09 | 783 | 533 | 2,504 | 1,704 |
| 0.1 | 810 | 603 | 2,592 | 1,928 |
| 0.2 | 960 | 793 | 3,072 | 2,536 |
| 0.3 | 1,110 | 1,043 | 3,552 | 3,336 |
| 0.4 | 1,273 | 1,389 | 4,072 | 4,445 |
| 0.5 | 1,435 | 1,539 | 4,592 | 4,925 |
| 0.6 | 1,520 | 1,796 | 4,864 | 5,747 |
| 0.7 | 1,605 | 2,049 | 5,136 | 6,557 |
| 0.8 | 1,735 | 2,138 | 5,552 | 6,840 |
| 0.9 | 1,865 | 2,559 | 5,968 | 8,189 |
| 1 | 1,980 | 2,896 | 6,336 | 9,267 |
| 2 | 3,035 | 4,399 | 9,712 | 14,075 |
| 3 | 3,920 | 5,839 | 12,543 | 18,685 |
| 4 | 4,805 | 6,923 | 15,375 | 22,152 |
| 5 | 5,537 | 7,750 | 17,719 | 24,799 |
| 6 | 6,270 | 7,906 | 20,064 | 25,299 |
| 7 | 6,790 | 8,886 | 21,728 | 28,435 |
| 8 | 7,310 | 8,218 | 23,392 | 26,299 |
| 9 | 7,705 | 8,375 | 24,656 | 26,799 |
| 10 | 8,100 | 9,699 | 25,920 | 31,037 |

TABLE 6-continued

Simulated TRTs for 10,000-member and 32,000-member populations using 16-sample and 32-sample pools

| Infection Rate (IR) (%) | Total Tests Required (TRT) | | | |
|---|---|---|---|---|
| | Total Population Size = 10,000 | | Total Population Size = 32,000 | |
| | Pool Size = 16 | Pool Size = 32 | Pool Size = 16 | Pool Size = 32 |
| 13 | 9,000 | 10,013 | 28,800 | 32,040 |
| 16 | 9,590 | 10,188 | 30,688 | 32,600 |
| 19 | 9,960 | 10,283 | 31,872 | 32,904 |
| 22 | 10,220 | 10,286 | 32,704 | 32,915 |
| 25 | 10,370 | 10,309 | 33,184 | 32,989 |

As can be seen from Table 6 for the 10,000-member population, somewhere between an infection rate of 0.3% and 0.4%, the simulator predicts that the optimal pool size (in terms of TRT) will shift from 32-sample pools to 16-sample pools. In other words, at all tested infection rates of 0.3% and lower, a 32-sample pooled sample testing scheme is predicted to provide a lower TRT than a 16-sample pooled sample testing scheme, and at all tested infection rates of 0.4% and higher, a 16-sample pooled sample testing scheme is predicted to provide a lower TRT than a 32-sample pooled sample testing scheme. Also, the results in Table 6 demonstrate for the 10,000-member population that a 16-sample pooled sample testing scheme is predicted to provide a lower TRT than a single sample testing scheme (i.e., where the TRT=10,000) for all infection rates up to at least 19%, and a 32-sample pooled sample testing scheme is predicted to provide a lower TRT than a single sample testing scheme for all infection rates up to at least 10%.

As seen in Table 6, the results for the 32,000-member population likewise demonstrate a shift in most efficient testing scheme (in terms of TRT) from the 32-sample polled sample testing scheme to the 16-sample pooled sample testing scheme between 0.3% and 0.4% infection rates. Likewise, the results for the 32,000-member population demonstrate a 16-sample pooled sample testing scheme is predicted to provide a lower TRT than a single sample testing scheme (i.e., where the TRT=32,000) for all infection rates up to at least 19%, and a 32-sample pooled sample testing scheme is predicted to provide a lower TRT than a single sample testing scheme for all infection rates up to at least 10%. These results confirm the theoretical expectation that optimal pool size is independent of total population size. Accordingly, simulations for large scale populations may be used to make predictions and testing choices for smaller scale populations.

Figure 6A:
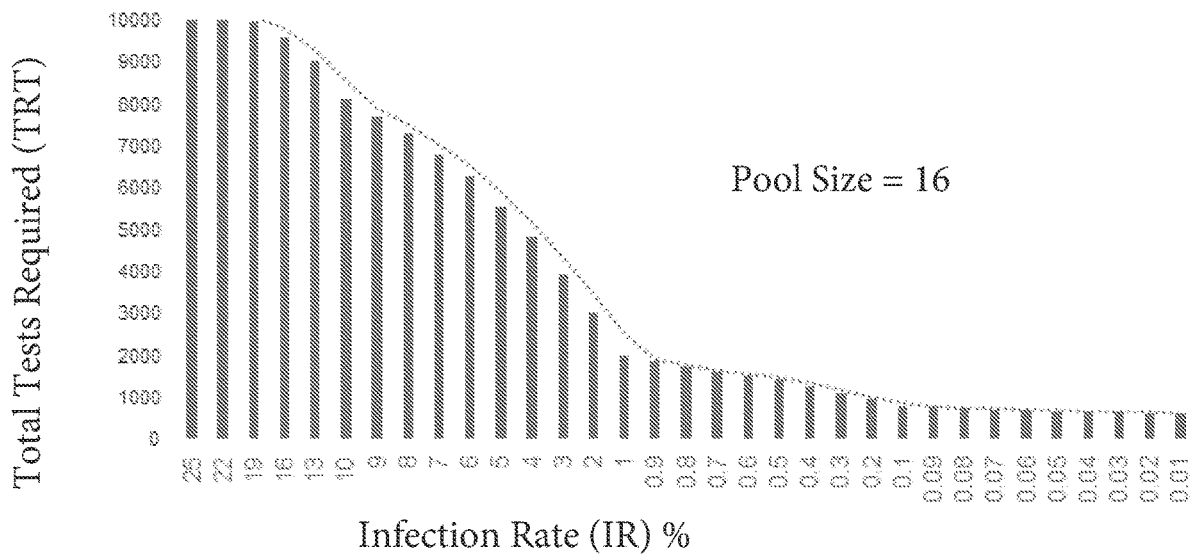
FIGS. 6A and 6B depict the simulated average total required tests (TRT) for performing member-specific testing on a simulated population of 10,000 individuals using hierarchies each comprising a single pooled sample across various infection rates from 0-25%.
Figure 6B:
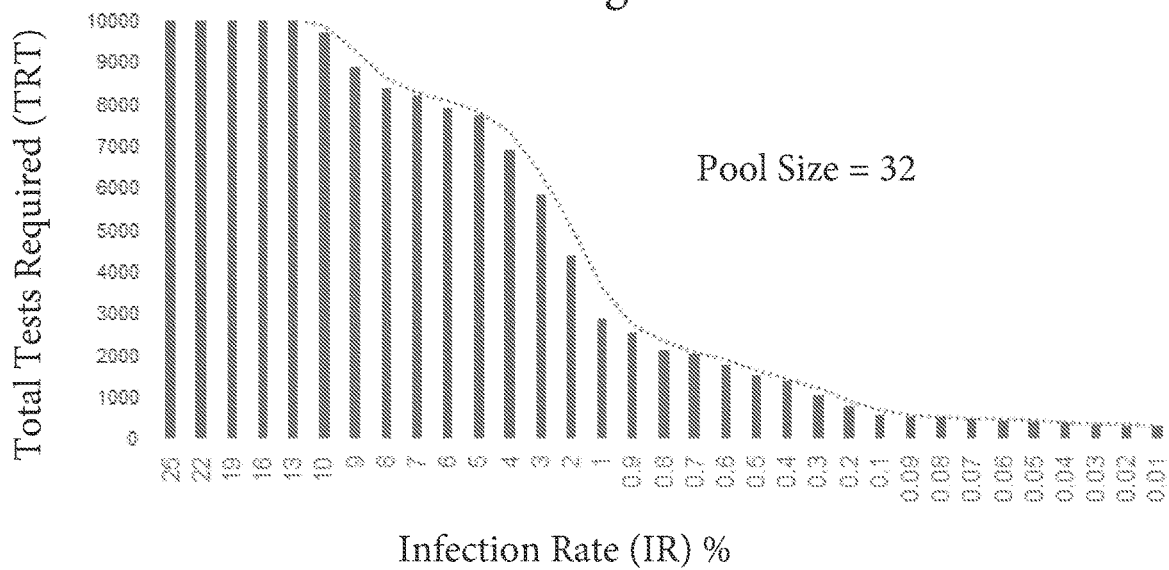

The simulated TRTs for the 10,000-member population are graphically illustrated across the tested infection rates in FIGS. 6A and 6B for 16-sample pools and 32-sample pools respectively. The costs saved can be determined from this data by calculating the TRT by the costs of any given assay test, which may be, for example, about $20, $25, $40, $50, or $80 USD. Based on these simulations, it was determined that a pooled sample testing scheme may generally not provide a lower TRT for any size population where the estimated infection rate is greater than 25%, at least with a 16-sample pool or 32 sample pool. The results have been verified to fall within the ranges expected by theoretical derivation of the multinomial (fifth-order) distribution and the averages close to the theoretical values.

Table 7 depicts simulated TRTs for the 10,000-member population at different pool sizes (4-sample, 8-sample, 16-sample, 32-sample, and 64-sample pools) for select infection rates. As can be seen from Table 7, the optimal pool size (based on TRT) shifts to increasingly smaller pool sizes as the infection rate increases. The 64-sample pool is optimal over 0-0.06%; the 32-sample pool is optimal over 0.07-0.2%; the 16-sample pool is optimal over 0.3-0.8%; the 8-sample pool is optimal over 0.9-4%, and the 4-person pool is optimal over at least 5-6% (possibly over 5% to about 19%, about 22%, about 25%, or about 30%, before single sample pooling becomes optimal).

TABLE 7

Simulated TRTs for various pool sizes

| Infection Rate (IR) (%) | Total Tests Required (TRT) for Various Pool Sizes (PS) | | | | |
|---|---|---|---|---|---|
| | PS = 64 | PS = 32 | PS = 16 | PS = 8 | PS = 4 |
| 0.01 | | 336 | 630 | | |
| 0.02 | | 346 | 635 | | |
| 0.03 | | 379 | 675 | | |
| 0.04 | | 399 | 680 | | |
| 0.05 | 417 | 419 | 693 | | |
| 0.06 | 468 | 473 | 705 | | |
| 0.07 | 519 | 503 | 730 | | |
| 0.08 | 571 | 533 | 755 | | |
| 0.09 | | 533 | 783 | | |
| 0.1 | | 603 | 810 | | |
| 0.2 | | 793 | 960 | | |
| 0.3 | | 1,043 | 1,110 | | |
| 0.4 | | 1,389 | 1,273 | | |
| 0.5 | | 1,539 | 1,435 | | |
| 0.6 | | 1,796 | 1,520 | | |
| 0.7 | | 2,049 | 1,605 | | |
| 0.8 | | 2,138 | 1,735 | 1,766 | |
| 0.9 | | 2,559 | 1,865 | 1,829 | |
| 1 | | 2,896 | 1,980 | 1,892 | |
| 2 | | 4,399 | 3,035 | 2,498 | |
| 3 | | 5,839 | 3,920 | 3,068 | 3,455 |
| 4 | | 6,923 | 4,805 | 3,607 | 3,758 |
| 5 | | 7,750 | 5,537 | 4,112 | 4,053 |
| 6 | | 7,906 | 6,270 | 4,586 | 4,340 |

TABLE 7-continued

Simulated TRTs for various pool sizes

| Infection Rate (IR) (%) | Total Tests Required (TRT) for Various Pool Sizes (PS) | | | | |
|---|---|---|---|---|---|
| | PS = 64 | PS = 32 | PS = 16 | PS = 8 | PS = 4 |
| 7 | | 8,886 | 6,790 | | |
| 8 | | 8,218 | 7,310 | | |
| 9 | | 8,375 | 7,705 | | |
| 10 | | 9,699 | 8,100 | | |
| 13 | | 10,013 | 9,000 | | |
| 16 | | 10,188 | 9,590 | | |
| 19 | | 10,283 | 9,960 | | |
| 22 | | 10,286 | 10,220 | | |
| 25 | | 10,309 | 10,370 | | |

The simulator may be adjusted for various cutoffs between classes of infection (i.e., defining different simulated classes of infected individuals). If the simulator assumes that all positive individuals will be detected, then only a distinction between infected and non-infected individuals is needed to perform the above simulations. The cutoffs can also be used to account for the different ability of different assays (e.g., having different LODs) to detect positive individuals at various ranges of viral density. For example, Table 8 below depicts the estimated capture rate for each of the above defined Frequency Classes for a specific assay. The capture rate may be defined as the percentage of positive samples within a class that the assay will properly identify (i.e., capture) as positive. The single sample LOD and/or capture rate data may be obtainable directly from the manufacturer for a specific assay. The pooled sample capture rate may likewise be obtainable from the manufacturer and/or calculated as described elsewhere herein. Where the capture rate is indicated as "<LOD" the capture rate may be presumed by the simulator to be effectively 0%. The simulator assumes no false positives (i.e., a capture rate of 0% for non-infected individuals) but could be adjusted to replicate the false positive rate of an assay. Repeated mass testing of the population can also significantly reduce false positives.

TABLE 8

Capture rates for different infection classes at various pool sizes

| Class | | Class Range | | Class Probability | | Est. Capture % 25-Sample | |
|---|---|---|---|---|---|---|---|
| | | Log10 | | | | | |
| Freq | Simulator | GCE/mL | GCE/mL | Freq Class | Simulator Class | Single Sample | Pooled Sample |
| 1 | Black | 0.25-0.75 | 2-6 | 0.000 | 0.117 | <LOD | <LOD |
| 2 | | 0.75-1.25 | 6-18 | 0.009 | | 95% | <LOD |
| 3 | | 1.25-1.75 | 18-56 | 0.021 | | 100% | <LOD |
| 4 | | 1.75-2.25 | 56-178 | 0.034 | | 100% | <LOD |
| 5 | | 2.25-2.75 | 178-562 | 0.052 | | 100% | >70% |
| 6 | Brown | 2.75-3.25 | 562-1778 | 0.056 | 0.056 | 100% | 100% |
| 7 | Blue | 3.25-3.75 | 1778-5623 | 0.056 | 0.056 | 100% | 100% |
| 8 | Red | >3.75 | >5623 | 0.771 | 0.771 | 100% | 100% |
| 9 | Green | | Non-infected | | | ~0% | ~0% |

The Simulator Classes for infected individuals (e.g., Black, Brown, Blue, Red) may be adjusted from those used in Table 8 to simplify accounting for the effect of the assay capture rate on the calculation of TRT during the simulation. For example, based on Table 8, adjustments to the Simulator Class cutoffs are made as depicted in Table 9 below.

TABLE 9

Alternative simulator class definitions

| Freq | Class Simulator | Class Range Log10 GCE/mL | GCE/mL | Class Probability Freq Class | Simulator Class | Est. Capture % 25-Sample Single Sample | Pooled Sample |
|---|---|---|---|---|---|---|---|
| 1 | Black | 0.25-0.75 | 2-6 | 0.000 | 0.065 | <LOD | <LOD |
| 2 |  | 0.75-1.25 | 6-18 | 0.009 |  | 95% | <LOD |
| 3 |  | 1.25-1.75 | 18-56 | 0.021 |  | 100% | <LOD |
| 4 |  | 1.75-2.25 | 56-178 | 0.034 |  | 100% | <LOD |
| 5 | Blue | 2.25-2.75 | 178-562 | 0.052 | 0.052 | 100% | >70% |
| 6 | Red | 2.75-3.25 | 562-1778 | 0.056 | 0.883 | 100% | 100% |
| 7 |  | 3.25-3.75 | 1778-5623 | 0.056 |  | 100% | 100% |
| 8 |  | >3.75 | >5623 | 0.771 |  | 100% | 100% |
| 9 | Green |  | Non-infected |  |  | ~0% | ~0% |

The simulations are performed as described above but independently assigning simulated infected individuals to one of the redefined Black, Blue, and Red classes of Table 9, based on the Simulator Class Probability. The simulated individuals are randomly distributed into pools and the frequency of each type of potential distribution (based on number of individuals in each Simulator Class) is tallied as described above. Based on the capture rate at the pooled sample size, the simulator determines whether any identifiable positive individuals are within the pool. For instance, based on Table 9, a 25-sample pool comprising a single individual from Class Black would be deemed unidentifiable and the simulator would simulate a negative pool result (a TRT of 1) and tally one false negative. A 25-sample pool comprising at least one individual from Class Blue or Class Red would be deemed identifiable and the simulator would simulate a positive pool results (a TRT of 25+1=26) and tally one false negative for each individual assigned to Class Black. The simulator may employ specific rules for pool distributions comprising no individuals from Class Blue and Class Red, but two or more individuals from Class Black (e.g., the pool result is positive if at least 3 Class Black individuals are present in the pool, etc.). The simulator tallies the total TRT for the population and the total false negatives for the population.

The simulator may assume a binary 100% or 0% capture rate. Alternatively, where a capture rate between 0-100% is available, the simulator may use a random number generator weighted by the capture rate probability to make an independent capture call for each relevant sample (e.g., the simulator will identify a 25-member pool comprising 1 Blue Class infection and no other infections as positive approximately 70% of the time and negative (with one false negative) approximately 30% of the time, based on Table 9). The simulator may similarly simulate single sample testing of the population so that the false negative rate may be compared between single sample testing and pooled sample testing, as well as between pooled sample testing of various pool sizes.

As used herein, the singular forms "a," "an," and "the" designate both the singular and the plural, unless expressly stated to designate the singular only.

The term "about" means that the number comprehended is not limited to the exact number set forth herein, and is intended to refer to numbers substantially around the recited number while not departing from the scope of the invention. As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

The above disclosure is made to illustrate the invention, but it should be understood that the invention is not limited to the specific conditions or details set forth above.

What is claimed is:

1. A method of testing a plurality of individuals within a population for an infection, the method comprising:
 a) obtaining an estimate of the infection rate within the population;
 b) obtaining a limit of detection for an assay used to test for the infection and selecting one or more pool sizes based on a maximum pool size determined from the limit of detection, the one or more pool sizes being no greater than the maximum pool size;
 c) for each of the one or more pool sizes, using a processing device to characterize a solution space specific to the estimated infection rate for a number of tests needed to identify individuals within the population who are positive for the infection using a pooled sample testing scheme, wherein characterizing the solution space comprises obtaining an expected number of tests needed;
 d) using the processing device to automatically choose a testing scheme based on the expected number of tests needed for each of the one or more pool sizes and automatically generate testing instructions that are configured to program a programmable sample preparation device, wherein choosing the testing scheme comprises determining that the expected number of tests for a chosen pool size is less than the number of individuals being tested and the chosen testing scheme comprises a pooled sample testing scheme defined by the chosen pool size, wherein the chosen pool size is one of the one or more pool sizes, and wherein the testing instructions comprise the chosen pool size;
 e) using the processing device to transmit the testing instructions to the sample preparation device;

f) using the sample preparation device to prepare pooled samples derived from biological specimens collected from the plurality of individuals according to the transmitted testing instructions, the sample preparation device being programmed by the transmitted testing instructions, wherein the sample preparation device comprises robotic pipetting or liquid handling machinery; and g) testing samples with the assay according to the chosen testing scheme, wherein testing the samples comprises using the assay to test pooled samples prepared by the sample preparation device.

2. The method of claim 1, wherein the one or more pool sizes comprises a plurality of pool sizes.

3. The method of claim 1, wherein the chosen testing scheme comprises a pooled sample testing scheme having a hierarchy having at least one level of mini-pools and the testing instructions comprise a structure of the hierarchy.

4. The method of claim 1, wherein characterizing the solution space comprises accessing one or more taxonomy tables of solution spaces stored on an electronic database.

5. The method of claim 1, wherein the chosen testing scheme comprises a pooled sample testing scheme in which the plurality of individuals is divided into two or more pools of the chosen pool size at a highest level of the pooled sample testing scheme.

6. The method of claim 1, wherein obtaining an expected number of tests needed comprises obtaining an average number of tests needed to identify the positive individuals, wherein the average number was determined by a simulation of the pooled sample testing scheme for the one or more pool sizes.

7. The method of claim 6, further comprising performing the simulation, wherein performing the simulation comprises:

a) simulating an infection status for each member of a simulated population having at least the same number of members as the plurality of individuals, wherein each simulated individual is assigned a positive or negative infection status based on a probability set by the estimated infection rate, and wherein assigning each simulated individual a positive or negative status comprises independently assigning the positive or negative infection status to each individual based on a probability set by the estimated infection rate;

b) randomly distributing the simulated individuals into simulated pools defined by the one or more pool sizes; and c) for each of the one or more pool sizes, determining a number of tests that would be needed to identify the simulated positive individuals using a pooled testing strategy defined by the pool size.

8. The method of claim 7, further comprising for each simulated positive individual, independently assigning a simulated infection level from two or more infection levels based on a probability determined from a known distribution of infection levels, wherein a lower portion of the distribution comprising between about 10% and about 35% of a range of the distribution, comprises at least two infection levels.

9. The method of claim 8, wherein performing the simulation further comprises identifying and tallying false negatives based on the simulated infection levels within each simulated pool and a predetermined adjusted limit of detection for the pool size, wherein identifying false negatives comprises assigning a false negative status to the simulated individual and/or simulated pool if the simulated infection level for the individual and/or pool is below the assay's limit of detection and/or adjusted limit of detection, respectively.

10. The method of claim 1, further comprising sorting each of the individuals within the plurality of individuals into pools based on a relative probability of infection in a manner that would minimize the number of tests needed to identify each positive individual assuming that the ranking of the individuals by their relative probabilities of infection would confine all the positive individuals to either a top portion or lower portion of the rankings.

11. The method of claim 10, wherein the relative probability of infection is calculated according to one or more factor values obtained for each of the individuals within the plurality of individuals, the one or more factor values relating to one or more of personal health, symptoms of infection, risk of exposure, and demographic information.

12. The method of claim 1, further comprising:
using the processing device to automatically associate unique sample identifiers associated with the biological specimens collected from each of the individuals within the plurality of individuals with unique patient identifiers.

13. The method of claim 1, further comprising using a processing device to automatically perform contact tracing within the population based on identification of positive individuals within the population and a database of individuals within the population.

14. The method of claim 1, wherein the estimated infection rate was determined from testing for the infection performed on a random selection of individuals within the population, wherein the assay used for testing had a limit of detection no greater than about 200 copies/mL.

15. The method of claim 1, wherein obtaining an expected number of tests needed comprises obtaining a minimum number of tests needed and/or a maximum number of tests needed.

16. The method of claim 11, wherein the one or more factor values were determined based on the responses of the individuals to one or more questions.

17. The method of claim 11, wherein the one or more factor values are weighted and the relative probability of infection is calculated as the sum of the one or more weighted factor values.

18. The method of claim 1, wherein the pooled sample testing scheme for one or more pool sizes comprises pooling the samples into pools having a total of $2^n$ individuals, n being greater than or equal to 3, and a plurality of mini-pools, wherein each pool is divided into two downstream mini-pools, and each mini-pool is divided into two additional downstream mini-pools except that mini-pools of 4 individuals are positioned directly upstream of the individual samples.

19. The method of claim 12, wherein the testing instructions comprise instructions for which biological specimens should be pooled together.

20. The method of claim 12, the method further comprising using the processing device to automatically associate positive or negative statuses with each unique sample identifier and/or each unique patient identifier based on received test results, wherein the processing device is programmed to associate unique sample identifiers with unique positions in the pooled sample testing scheme.

* * * * *